United States Patent
Autran et al.

(10) Patent No.: US 9,072,633 B2
(45) Date of Patent: Jul. 7, 2015

(54) BIAXIALLY STRETCHABLE OUTER COVER FOR AN ABSORBENT ARTICLE

(75) Inventors: Jean-Philippe Marie Autran, Wyoming, OH (US); Donald Carroll Roe, West Chester Township, OH (US); Terrill Alan Young, Cincinnati, OH (US); Joan Helen Mooney, Reading, OH (US); Fred Naval Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 585 days.

(21) Appl. No.: 11/599,829

(22) Filed: Nov. 15, 2006

(65) Prior Publication Data

US 2007/0287348 A1 Dec. 13, 2007

Related U.S. Application Data

(60) Provisional application No. 60/811,580, filed on Jun. 7, 2006.

(51) Int. Cl.
*A61F 13/15* (2006.01)
*B32B 5/26* (2006.01)
(Continued)

(52) U.S. Cl.
CPC ............. *A61F 13/51478* (2013.01); *B32B 5/26* (2013.01); *B32B 5/022* (2013.01); *B32B 2250/20* (2013.01); *B32B 2307/51* (2013.01); *B32B 2555/02* (2013.01); *A61F 13/51464* (2013.01)

(58) Field of Classification Search
CPC ................... A61F 13/51464; A61F 13/51478; A61F 13/537; A61F 2013/49057; A61F 2013/51322; A61F 2013/51429; D04H 1/42; D04H 3/00; D04H 3/14; D04H 13/00; D04H 3/147; D01F 8/06; D01F 8/16; D01D 5/0084; D01D 5/08; D01D 5/082; D01D 5/30
USPC ................. 442/334, 339, 340–353, 400, 401, 442/361–364, 381, 382; 428/372, 373
See application file for complete search history.

(56) References Cited

U.S. PATENT DOCUMENTS 3,692,618 A 9/1972 Dorschner et al.
3,802,817 A 4/1974 Matsuki et al.
(Continued)

FOREIGN PATENT DOCUMENTS

EP 0 630 630 A2 12/1994
EP 1 559 388 A2 8/2005
(Continued)

OTHER PUBLICATIONS

U.S. Appl. No. 11/599,862, filed Nov. 15, 2006, Lodge et al.
(Continued)

*Primary Examiner* — Jennifer A Steele
(74) *Attorney, Agent, or Firm* — Kathleen Y. Carter; John G. Powell

(57) ABSTRACT

An outer cover for use with an absorbent article having a layer of nonwoven fibrous material and optionally including a polymeric layer laminated or printed onto the layer of nonwoven fibrous material. The outer cover includes at least one plastic component and at least one elastic component in the nonwoven fibrous material and/or optional polymeric layer. The outer cover can have different structural combinations of spunbond fibers, meltblown fibers, and/or nanofibers. The combination of plastic and elastic components results in an outer cover that has favorable mechanical, physical, and aesthetic properties. The outer cover can be rendered either uniaxially or biaxially stretchable via a mechanical activation process.

23 Claims, 8 Drawing Sheets

(51) Int. Cl.
  *D04H 1/00* (2006.01)
  *A61F 13/514* (2006.01)
  *B32B 5/02* (2006.01)

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague | |
| 3,929,135 A | 12/1975 | Thompson | |
| 4,116,892 A | 9/1978 | Schwarz | |
| 4,200,963 A | 5/1980 | Kamfe et al. | |
| 4,209,563 A * | 6/1980 | Sisson | 442/329 |
| 4,223,063 A | 9/1980 | Sabee | |
| 4,324,246 A | 4/1982 | Mullane et al. | |
| 4,340,563 A | 7/1982 | Appel et al. | |
| 4,342,314 A | 8/1982 | Radel et al. | |
| 4,438,167 A | 3/1984 | Schwarz | |
| 4,463,045 A | 7/1984 | Ahr et al. | |
| 4,515,595 A | 5/1985 | Kievit et al. | |
| 4,525,407 A | 6/1985 | Ness | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,655,760 A | 4/1987 | Morman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,621 A | 10/1987 | Stevens et al. | |
| 4,701,171 A | 10/1987 | Boland et al. | |
| 4,701,172 A | 10/1987 | Stevens | |
| 4,701,173 A | 10/1987 | Zehner et al. | |
| 4,701,174 A | 10/1987 | Johnson | |
| 4,701,175 A | 10/1987 | Boland et al. | |
| 4,718,900 A | 1/1988 | Boland et al. | |
| 4,756,709 A | 7/1988 | Stevens | |
| 4,770,656 A | 9/1988 | Proxmire et al. | |
| 4,785,996 A | 11/1988 | Ziecker et al. | |
| 4,795,454 A | 1/1989 | Dragoo | |
| 4,801,494 A | 1/1989 | Datta et al. | |
| 4,834,735 A | 5/1989 | Alemany et al. | |
| 4,834,738 A | 5/1989 | Kielpikowski et al. | |
| 4,834,741 A | 5/1989 | Sabee | |
| 4,838,885 A | 6/1989 | Bernardin | |
| 4,842,666 A | 6/1989 | Werenicz | |
| 4,846,815 A | 7/1989 | Scripps | |
| 4,850,990 A | 7/1989 | Huntoon et al. | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,143,679 A | 9/1992 | Weber et al. | |
| 5,147,345 A | 9/1992 | Young et al. | |
| 5,151,092 A | 9/1992 | Buell et al. | |
| 5,156,793 A | 10/1992 | Buell et al. | |
| 5,167,897 A | 12/1992 | Weber et al. | |
| 5,171,236 A | 12/1992 | Dreier et al. | |
| 5,171,239 A | 12/1992 | Igaue et al. | |
| 5,202,173 A | 4/1993 | Wu et al. | |
| 5,221,274 A | 6/1993 | Buell et al. | |
| 5,230,949 A * | 7/1993 | Howard et al. | 442/365 |
| 5,246,433 A | 9/1993 | Hasse et al. | |
| 5,254,111 A | 10/1993 | Cancio et al. | |
| 5,260,345 A | 11/1993 | DesMarais et al. | |
| 5,269,775 A | 12/1993 | Freeland et al. | |
| 5,296,184 A | 3/1994 | Wu et al. | |
| 5,306,266 A | 4/1994 | Freeland | |
| 5,330,458 A | 7/1994 | Buell et al. | |
| 5,342,338 A | 8/1994 | Roe | |
| 5,354,597 A | 10/1994 | Capik et al. | |
| 5,366,782 A | 11/1994 | Curro et al. | |
| 5,387,207 A | 2/1995 | Dyer et al. | |
| 5,397,318 A | 3/1995 | Dreier | |
| 5,422,172 A | 6/1995 | Wu | |
| 5,439,458 A * | 8/1995 | Noel et al. | 604/378 |
| 5,460,622 A | 10/1995 | Dragoo et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,569,234 A | 10/1996 | Buell et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,626,571 A * | 5/1997 | Young et al. | 604/370 |
| 5,635,191 A | 6/1997 | Roe et al. | |
| 5,643,588 A | 7/1997 | Roe et al. | |
| 5,650,214 A | 7/1997 | Anderson et al. | |
| 5,653,703 A | 8/1997 | Roe et al. | |
| 5,709,747 A | 1/1998 | Goldwasser | |
| 5,709,921 A * | 1/1998 | Shawver | 428/152 |
| 5,865,823 A | 2/1999 | Curro | |
| 5,885,656 A | 3/1999 | Goldwasser | |
| 5,897,545 A | 4/1999 | Kline et al. | |
| 5,938,648 A | 8/1999 | LaVon et al. | |
| 5,941,864 A | 8/1999 | Roe | |
| 5,957,908 A | 9/1999 | Kline et al. | |
| 5,968,025 A | 10/1999 | Roe et al. | |
| 5,977,430 A | 11/1999 | Roe et al. | |
| 5,997,520 A | 12/1999 | Ahr et al. | |
| 6,013,589 A | 1/2000 | DesMarais et al. | |
| 6,120,487 A | 9/2000 | Ashton | |
| 6,120,489 A | 9/2000 | Johnson et al. | |
| 6,168,584 B1 | 1/2001 | Allen et al. | |
| 6,169,151 B1 | 1/2001 | Waymouth et al. | |
| 6,177,607 B1 * | 1/2001 | Blaney et al. | 604/378 |
| 6,183,847 B1 | 2/2001 | Goldwasser | |
| 6,193,701 B1 | 2/2001 | Van Gompel et al. | |
| 6,258,308 B1 | 7/2001 | Brady et al. | |
| 6,368,444 B1 | 4/2002 | Jameson et al. | |
| 6,417,121 B1 * | 7/2002 | Newkirk et al. | 442/364 |
| 6,432,098 B1 | 8/2002 | Carlucci et al. | |
| 6,436,080 B1 * | 8/2002 | Carlucci et al. | 604/385.01 |
| 6,476,289 B1 | 11/2002 | Buell et al. | |
| 6,518,378 B2 | 2/2003 | Waymouth et al. | |
| 6,521,555 B1 | 2/2003 | Bodaghi et al. | |
| 6,555,643 B1 | 4/2003 | Rieger | |
| 6,559,262 B1 | 5/2003 | Waymouth et al. | |
| 6,663,611 B2 * | 12/2003 | Blaney et al. | 604/385.01 |
| 6,680,265 B1 * | 1/2004 | Smith et al. | 442/401 |
| 6,680,422 B2 | 1/2004 | Roe | |
| 6,716,441 B1 | 4/2004 | Osborne et al. | |
| 6,766,817 B2 | 7/2004 | da Silva | |
| 6,794,023 B1 | 9/2004 | Melik et al. | |
| 6,811,643 B2 | 11/2004 | McAmish et al. | |
| 6,821,612 B1 | 11/2004 | Melik et al. | |
| 6,843,949 B2 | 1/2005 | Brady et al. | |
| 6,918,404 B2 | 7/2005 | Dias da Silva | |
| 6,926,704 B2 * | 8/2005 | Andersson et al. | 604/385.13 |
| 6,936,039 B2 | 8/2005 | Kline et al. | |
| 6,969,378 B1 * | 11/2005 | Vukos et al. | 604/385.22 |
| 7,056,411 B2 | 6/2006 | Desai et al. | |
| 7,066,586 B2 | 6/2006 | da Silva | |
| 7,169,288 B2 | 1/2007 | Drapeau | |
| 7,201,822 B2 | 4/2007 | Schneider et al. | |
| 7,222,654 B2 | 5/2007 | Schneider et al. | |
| 7,223,818 B2 | 5/2007 | Autran et al. | |
| 7,390,760 B1 * | 6/2008 | Chen et al. | 442/341 |
| 2002/0105110 A1 | 8/2002 | Dobrin et al. | |
| 2002/0112276 A1 | 8/2002 | Ruman et al. | |
| 2002/0124953 A1 * | 9/2002 | Sennett et al. | 156/273.1 |
| 2003/0129909 A1 | 7/2003 | Zucker | |
| 2003/0225382 A1 | 12/2003 | Tombult-Meyer et al. | |

(56) References Cited

U.S. PATENT DOCUMENTS

| | | |
|---|---|---|
| 2003/0233082 A1 | 12/2003 | Kline et al. |
| 2004/0002691 A1 | 1/2004 | Popp et al. |
| 2004/0039364 A1 | 2/2004 | Karami |
| 2004/0092677 A1 | 5/2004 | Hanke et al. |
| 2004/0116028 A1* | 6/2004 | Bryner .................... 442/381 |
| 2004/0167486 A1 | 8/2004 | Busam et al. |
| 2004/0181200 A1* | 9/2004 | Desai et al. .............. 604/385.16 |
| 2004/0193133 A1 | 9/2004 | Desai et al. |
| 2004/0222553 A1 | 11/2004 | Desai et al. |
| 2004/0224132 A1 | 11/2004 | Roe et al. |
| 2004/0238105 A1 | 12/2004 | Schneider et al. |
| 2005/0070866 A1 | 3/2005 | Isele et al. |
| 2005/0164586 A1 | 7/2005 | Autran et al. |
| 2005/0165173 A1 | 7/2005 | Autran et al. |
| 2005/0211368 A1 | 9/2005 | McGuire et al. |
| 2005/0214461 A1 | 9/2005 | Desai et al. |
| 2005/0215963 A1 | 9/2005 | Autran et al. |
| 2005/0215964 A1 | 9/2005 | Autran et al. |
| 2005/0230034 A1 | 10/2005 | Arora et al. |
| 2006/0014460 A1 | 1/2006 | Isele et al. |
| 2006/0084339 A1* | 4/2006 | Webb et al. ................... 442/329 |
| 2006/0155253 A1 | 7/2006 | Dziezok et al. |
| 2006/0155254 A1 | 7/2006 | Sanz et al. |
| 2006/0247593 A1* | 11/2006 | Sperl et al. ............... 604/385.22 |
| 2007/0078427 A1 | 4/2007 | Raycheck et al. |
| 2007/0093769 A1 | 4/2007 | Kline et al. |
| 2008/0004591 A1 | 1/2008 | Desai et al. |
| 2008/0224351 A1 | 9/2008 | Curro et al. |

FOREIGN PATENT DOCUMENTS

| | | |
|---|---|---|
| EP | 1 600 132 A1 | 11/2005 |
| JP | 2000-328420 A | 11/2000 |
| JP | 2004-330692 A | 11/2004 |
| JP | 2005-171456 A | 6/2005 |
| JP | 2006-045291 A | 2/2006 |
| WO | WO 94/14395 A1 | 7/1994 |
| WO | WO 95/16746 A1 | 6/1995 |
| WO | WO 95/24173 A2 | 9/1995 |
| WO | WO 98/14156 A | 4/1998 |
| WO | WO 00/29199 A1 | 5/2000 |
| WO | WO 01/30564 A1 | 5/2001 |
| WO | WO 03/072338 A1 | 9/2003 |
| WO | WO 2005/110748 A1 | 11/2005 |
| WO | WO 2008/067463 A1 | 6/2008 |

OTHER PUBLICATIONS

U.S. Appl. No. 11/599,851, filed Nov. 15, 2006, Lodge et al.
U.S. Appl. No. 11/599,852, filed Nov. 15, 2006, Roe et al.
International Search Report mailed on Jun. 12, 2007, 3 pages.

* cited by examiner

BIAXIALLY STRETCHABLE OUTER COVER FOR AN ABSORBENT ARTICLE

CROSS REFERENCE TO RELATED APPLICATIONS

This application claims the benefit of U.S. Provisional Application No. 60/811,580, filed Jun. 7, 2006, which is incorporated herein by reference.

FIELD OF THE INVENTION

The present invention generally relates to absorbent articles, and stretchable outer covers used therewith. More specifically, the present invention relates to the materials and methods for various biaxially stretchable outer cover configurations having favorable mechanical properties (e.g., strength, elasticity), barrier properties (e.g., liquid impermeability, breathability), and visual properties (e.g., opacity).

BACKGROUND OF THE INVENTION

Absorbent articles such as conventional taped diapers, pull-on diapers, training pants, incontinence briefs, and the like, offer the benefit of receiving and containing urine and/or other bodily exudates. Such absorbent articles can include a chassis that defines a waist opening and a pair of leg openings. A pair of barrier leg cuffs can extend from the chassis toward the wearer adjacent the leg openings, thereby forming a seal with the wearer's body to improve containment of liquids and other body exudates. Conventional chassis include an absorbent core that is disposed between a topsheet and a garment-facing outer cover (also known as a backsheet).

The outer cover can include a stretchable waistband at one or both of its ends (e.g., proximal opposing laterally extending edges), stretchable leg bands surrounding the leg openings, and stretchable side panels, which additional components can be integral or separate discrete elements attached directly or indirectly to the outer cover. The remainder of the outer cover typically includes a non-stretchable nonwoven-breathable film laminate. Undesirably, however, these diapers sometimes do not conform well to the wearer's body in response to body movements (e.g. sitting, standing, and walking), due to the relative anatomic dimensional changes (which can, in some instances, be up to 50%) in the buttocks region caused by these movements. This conformity problem is further exacerbated because one diaper typically must fit many wearers of various shapes and sizes in a single product size.

The dimensions of the smallest and biggest wearers within a given product size range can be markedly different. For instance, in the case of wearers, the waist circumference at the navel can vary by 80 mm within a size range. Also, the navel-to-back distance, which is the distance from the navel, around the crotch, and to a point on the back of the wearer that is in the same horizontal plane as the navel, can vary by about 80 mm from the smallest to the largest wearers in this same size range.

In addition, many caregivers and wearers prefer the look and feel of cotton underwear not provided by conventional diapers. For instance, cotton underwear includes elastic waist and leg bands that encircle the waist and leg regions of the wearer and provide the primary forces that keep the underwear on the wearer's body. Furthermore, the cotton outer cover (except in the waist and leg bands) can be stretched along the width and length directions in response to a relatively low force to accommodate the anatomic dimensional differences related to movement and different wearer positions. The stretched portion returns back to substantially its original dimension once the applied force is removed. In other words, the cotton outer cover of the underwear exhibits low-force, recoverable biaxial stretch that provides a conforming fit to a wider array of wearer sizes than conventional diapers.

SUMMARY OF THE INVENTION

The outer covers of the present disclosure avoid the disadvantages of conventional outer covers and provide the advantages of cotton underwear. The outer covers generally include at least one plastic component and at least one elastomeric component, which components can be included in the outer cover in either or both of a nonwoven fibrous material and an optional polymeric film laminated or printed onto the nonwoven fibrous material. The combination of plastic and elastic components results in an outer cover that, once mechanically activated, has favorable mechanical, physical, and aesthetic properties, which properties make the outer cover suitable for inclusion in an absorbent article.

While the disclosed outer covers are generally described in relation to biaxially stretchable outer covers ("BSOCs"), the outer covers can also be uniaxially stretchable (for example in the cross direction), and the following description applies equally as well to uniaxially stretchable outer covers. The disclosed outer covers exhibit the low-force, recoverable biaxial stretch of cotton underwear, while maintaining the requisite levels of mechanical strength and liquid impermeability for an absorbent article outer cover. The disclosed outer covers may also be breathable and have a high opacity. The favorable biaxial stretch properties of the disclosed outer covers result in absorbent articles that conform well to an individual wearer's body in response to body movements. Further, these biaxial stretch properties permit an absorbent article (e.g., a diaper) manufactured in a single product size to comfortably accommodate a wider size range of consumers.

One aspect of the disclosure provides an outer cover for an absorbent article, including a first layer of nonwoven fibers having a first number-average fiber diameter, a second layer of fibers having a second number-average fiber diameter less than the first number-average fiber diameter, the second layer of fibers disposed on the first layer of nonwoven fibers, and, optionally, a polymeric layer disposed on the first or second layer of fibers. The nonwoven fibers of the first layer include at least one of elastomeric fibers, plastic fibers, a mixture of elastomeric fibers and plastic fibers, bi-component fibers, plastoelastic blend fibers, wherein each of the bi-component fibers and the plastoelastic blend fibers includes an elastomeric component and a plastic component. The polymeric layer includes an elastomeric layer, a plastic layer, or a plastoelastic blend layer including an elastomeric component and a plastic component. The outer cover includes at least one of the elastomeric fibers, the elastomeric component, and the elastomeric layer (which each independently include at least one elastomer chosen from an elastomeric polypropylene, and a styrenic block copolymer). The outer cover further includes at least one of the plastic fibers, the plastic component, and the plastic layer. In further embodiments, the outer cover can be rendered biaxially stretchable, and/or the outer cover can be incorporated into an absorbent article including a topsheet and an absorbent core disposed between the topsheet and the outer cover.

Another aspect of the disclosure provides an outer cover for an absorbent article including a first layer including spunbond fibers, a second layer including meltblown fibers disposed on the first layer; a third layer including nanofibers disposed on the second layer, and a fourth layer including meltblown fibers disposed on the third layer. The fibers of the first layer include at least one of a mixture of elastomeric fibers and plastic fibers, bi-component fibers, and plastoelastic blend fibers, wherein each of the bi-component fibers and the plastoelastic blend fibers includes an elastomeric component and a plastic component. The fibers of the first layer include elastomeric fibers. The nanofibers of the third layer include at least one of elastomeric fibers and plastoelastic blend fibers. The fibers of the fourth layer include plastoelastic blend fibers. In a further embodiment, the outer cover further includes a fifth layer including spunbond or carded fibers disposed on the fourth layer, and the fibers of the fifth layer include at least one of plastic fibers and plastoelastic blend fibers. In another embodiment, the outer cover can be incorporated into an absorbent article including a topsheet and an absorbent core disposed between the topsheet and the outer cover.

By employing various types of the disclosed outer covers in connection with an absorbent article, the resulting article offers improved versatility and fit over those previously known in the art. These and other advantages of the present invention will become apparent in light of the description below.

Figure 1:
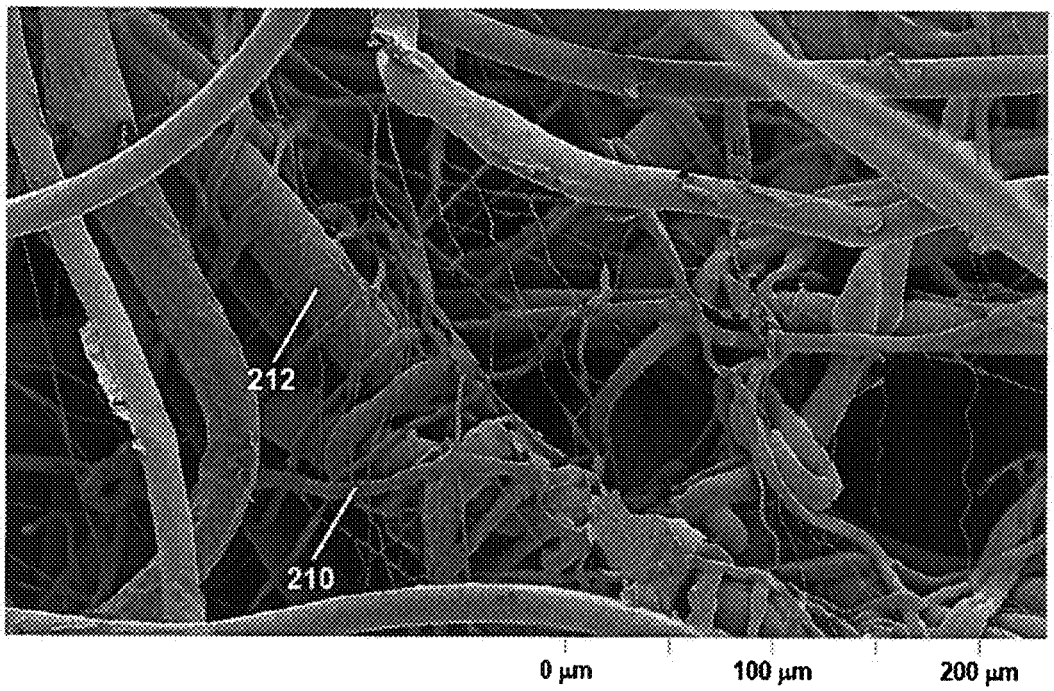
FIG. 1 is a scanning electron micrograph of a spunbond-meltblown-spunbond nonwoven material prior to mechanical activation.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Definitions

As used herein, the following terms shall have the meaning specified thereafter:

The term "disposable," as used herein in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

The term "absorbent article" as used herein refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" as used herein refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The terms "proximal" and "distal" as used herein refer respectively to the location of an element relatively near to or far from the center of a structure (e.g., the proximal edge of a longitudinally extending element is located nearer to the longitudinal axis than the distal edge of the same element is located relative to the same longitudinal axis).

The terms "body-facing," "inner-facing," "outer-facing," and "garment-facing" as used herein refer respectively to the relative location of an element or a surface of an element or group of elements. "Body-facing" and "inner-facing" imply the element or surface is nearer to the wearer's body during wear (i.e., closer to the wearer's body than a garment-facing surface or an outer-facing surface). "Garment-facing" and "outer-facing" imply the element or surface is more remote from the wearer during wear (i.e., element or surface is nearer to the wearer's garments that can be worn over the disposable absorbent article).

The term "longitudinal" as used herein refers to a direction running substantially perpendicular from a waist edge to an opposing waist edge of the article and generally parallel to the maximum linear dimension of the article. Directions within 45 degrees of the longitudinal direction are considered to be "longitudinal."

The term "lateral" as used herein refers to a direction running from a longitudinal edge to an opposing longitudinal edge of the article and generally at a right angle to the longitudinal direction. Directions within 45 degrees of the lateral direction are considered to be "lateral."

"Longitudinal centerline" refers to a longitudinal line that can be drawn through the middle of an absorbent article. For most absorbent articles, the longitudinal centerline separates the article into two substantially symmetrical halves that will fall on the left and right halves of a wearer during wear.

"Lateral centerline" refers to a lateral line drawn through the midpoint of the longitudinal centerline and perpendicular to the longitudinal centerline.

The terms "outboard" and "inboard" as used herein refer respectively to the location of an element disposed relatively far from or near to the longitudinal centerline of the diaper with respect to a second element. For example, if element A is outboard of element B, then element A is farther from the longitudinal centerline than is element B.

The term "machine direction" (also "MD" or "length direction") as applied to a film or nonwoven material, refers to the direction that was parallel to the direction of travel of the film or nonwoven as it was processed in the forming apparatus. The "cross machine direction" (also "CD" or "width direction") refers to the direction perpendicular to the machine direction and in the plane generally defined by the film or nonwoven material.

The term "disposed" as used herein refers to an element being positioned in a particular place with regard to another element. When one group of fibers is disposed on a second group of fibers, the first and second groups of fibers generally form a layered, laminate structure in which at least some fibers from the first and second groups are in contact with each other. In some embodiments, individual fibers from the first and/or second group at the interface between the two groups can be dispersed among the fibers of the adjacent group, thereby forming an at least partially intermingled, entangled fibrous region between the two groups. When a polymeric layer (for example a film) is disposed on a surface (for example a group or layer of fibers), the polymeric layer can be laminated to or printed on the surface.

"Joined" refers to configurations whereby an element is directly secured to another element by affixing the element directly to the other element and to configurations whereby an element is indirectly secured to another element by affixing the element to intermediate member(s) which in turn are affixed to the other element.

"Liquid-permeable" (or "liquid-pervious") and "liquid-impermeable" (or "liquid-impervious") refer to the penetrability of materials in the context of the intended usage of disposable absorbent articles. Specifically, "liquid permeable" refers to a layer or a layered structure having pores, openings, and/or interconnected void spaces that permit liquid water to pass through its thickness in the absence of a forcing pressure. Conversely, "liquid impermeable" refers to a layer or a layered structure through the thickness of which liquid water cannot pass in the absence of a forcing pressure. Liquid impermeable materials exhibit a hydrohead of at least about 5 mbar as measured according to the Hydrostatic Head Pressure ("hydrohead") provided below in the Test Methods. However, it may be desirable that a liquid impermeable material exhibit a hydrohead of at least about 10 mbar or about 15 mbar. A layer or a layered structure that is water-impermeable according to this definition may be vapor-permeable, for example permitting transmission of air and water vapor. Such a vapor-permeable layer or layered structure is commonly known in the art as "breathable."

As used herein, the term "stretchable" refers to materials which can stretch at least 5% on the upcurve of the hysteresis test at a load of about 400 gf/cm. The term "non-stretchable" refers to materials which cannot stretch at least 5% on the upcurve of the hysteresis test at a load of about 400 gf/cm.

The terms "elastic" and "elastomeric" as used herein are synonymous and refer to any material that upon application of a biasing force, can stretch to an elongated length of at least about 110% or even to 125% of its relaxed, original length (i.e. can stretch to 10% or even 25% more than its original length), without rupture or breakage. Further, upon release of the applied force, the material may recover at least about 40%, at least about 60%, or even at least about 80% of its elongation. For example, a material that has an initial length of 100 mm can extend at least to 110 mm, and upon removal of the force would retract to a length of 106 mm (i.e., exhibiting a 40% recovery). The term "inelastic" refers herein to a material that cannot stretch to 10% more than its original length without rupture or breakage.

The terms "extensible" and "plastic" as used herein are synonymous and refer to any material that upon application of a biasing force, can stretch to an elongated length of at least about 110% or even 125% of its relaxed, original length (i.e., can stretch to 10% or even 25% more than its original length), without rupture or breakage. Further, upon release of the applied force, the material shows little recovery, for example less than about 40%, less than about 20%, or even less than about 10% of its elongation.

The terms "plastoelastic" and "elastoplastic" as used herein are synonymous and refer to any material that has the ability to stretch in a substantially plastic manner during an initial strain cycle (i.e., applying a tensile force to induce strain in the material, then removing the force allowing the material to relax), yet which exhibits substantially elastic behavior and recovery during subsequent strain cycles. Plastoelastic materials contain at least one plastic component and at least one elastic component, which components can be in the form of polymeric fibers, polymeric layers, and/or polymeric mixtures (including, for example, bi-component fibers and polymeric blends including the plastic and elastic components). Suitable plastoelastic materials and properties are described in U.S. 2005/0215963 and U.S. 2005/0215964.

As used herein, the term "activated" refers to a material which has been mechanically deformed so as to impart elastic extensibility to at least a portion the material, such as, for example by incremental stretching.

The term "core assembly" as used herein refers to at least an absorbent core and other optional structures (e.g., barrier cuffs, liquid barrier layer, storage layer, acquisition layer, distribution layer, etc.) to enhance containment of waste and/or structures to enhance structural integrity.

The term "circumference" or "circumferential" as used herein, refers to a closed path on the surface around the torso of the body or around a leg. That path can have a smooth, continuous curvature, or it can have "corners" where the curvature makes an abrupt change, e.g. when the path passes through a connection zone with three or more connecting tension-carrying bands.

The terms "pant," "training pant," "pre-closed diaper," "pre-fastened diaper," "pull-on diaper," and "pant-like garment" as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat.

No. 5,092,861; U.S. Pat. No. 5,897,545; U.S. Pat. No. 5,957,908; and U.S. Patent Publication No. 2003/0233082 A1.

The term "spunbond fibers" refers to a nonwoven fiber fabric of small-diameter, continuous fibers that are formed by extruding a molten thermoplastic polymer into fibers from a plurality of capillaries of a spinneret. The extruded fibers are cooled to a non-tacky state while being drawn by an eductive or other well known drawing mechanism. The drawn fibers are deposited or laid onto a forming surface in a generally random, isotropic manner to form a loosely entangled fiber web, and then the laid fiber web is subjected to a bonding process to impart physical integrity and dimensional stability. The production of spunbond fabrics is disclosed, for example, in U.S. Pat. Nos. 3,802,817, 3,692,618, and 4,340,563. Typically, spunbond fibers have a linear density of about 2 denier to about 6 denier and diameters of about 10 µm to about 30 µm, although finer and heavier spunbond fibers can be produced. The number-average spunbond fiber diameter is generally in a range of about 10 µm to about 30 µm or about 15 µm to about 25 µm, for example about 18 µm (with a linear density of about 2.2 denier).

The term "meltblown fibers" refers to nonwoven fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Meltblown fibers are generally discontinuous microfibers, and are generally self-bonding when deposited onto a collecting surface. Meltblown fibers generally have diameters of about 1 µm to about 10 µm. The number-average meltblown fiber diameter is generally in a range of about 1 µm to about 10 µm or about 1 µm to about 5 µm.

"Nanofibers" are sub-micron diameter fibers formed according to the process outlined in U.S. 2005/0070866 and U.S. 2006/0014460. Nanofibers generally have diameters of about 0.1 µm to about 1 µm, although larger diameters are possible. The number-average nanofiber diameter is generally in a range of about 0.1 µm to about 1 µm, for example about 0.5 µm.

BSOC Including Plastoelastic Materials

General Description of the Embodiments

The BSOCs according to the present invention may include at least one elastic material and at least one plastic material. The BSOC may include a layer of nonwoven material and, optionally, a polymeric layer disposed on the nonwoven material. The nonwoven material and the polymeric layer can be formed (independently) from a plastoelastic material, an elastic material, or a plastic material. Although the BSOC may have at least one plastic material and at least one elastic material, the two components can be included in the BSOC in the form of a single plastoelastic material.

In a first embodiment, the BSOC does not include the polymeric layer, in which case the nonwoven material may be in the form of a plastoelastic material (i.e., it includes an elastomeric component and a plastic component). In a second embodiment, the BSOC may include the polymeric layer in the form of a polymeric film laminated to the nonwoven material. This second embodiment has three additional aspects in which: (1) a layer of plastoelastic nonwoven material is laminated to a plastic polymeric film, (2) a layer of plastoelastic nonwoven material is laminated to a plastoelastic polymeric film, and (3) a layer of plastic nonwoven material is laminated to a plastoelastic polymeric film. When both the nonwoven material and the polymeric film are formed from a plastoelastic material, they can be formed from either the same or different plastoelastic materials. In another embodiment, the BSOC includes a layer of nonwoven material, such as, for example a layer of plastic fibers, onto which an elastomeric layer is printed or laminated in the form of a pattern or film.

Polymeric Materials

The plastoelastic materials of the present invention, whether included in the nonwoven fibers or the polymeric layer, may include an elastomeric component and a plastic component. The components can be in the form of fibers (e.g., elastomeric fibers, plastic fibers), in the form of a polymeric layer (e.g., an elastomeric layer, a plastic layer), or as an element of a polymeric mixture (e.g., bi-component fibers, plastoelastic blend fibers, a plastoelastic blend layer). One plastoelastic material can be in the form of a plastoelastic blend of an elastomeric component and a plastic component. The plastoelastic blend can form either a heterogeneous or a homogeneous polymeric mixture, depending upon the degree of miscibility of the elastomeric and plastic components. For heterogeneous mixtures, the resultant stress-strain properties of the plastoelastic material may be improved when micro-scale dispersion of any immiscible components is achieved (i.e., any discernable discrete domains of pure elastomeric component or pure plastic component have an equivalent diameter less than about 10 microns). Suitable blending means are known in the art and include a twin screw extruder (e.g., POLYLAB twin screw extruder, available from Thermo Electron, Karlsruhe, Germany). If the plastoelastic blend forms a heterogeneous mixture, one component can form a continuous phase that encloses dispersed particles of the other component. Another example of a plastoelastic material includes plastoelastic bi-component fibers, in which a single fiber has discrete regions of the elastomeric and plastic components in, for example, a core-sheath (or, equivalently, a core-shell) or a side-by-side arrangement. Another example of a plastoelastic material includes mixed fibers, in which some fibers are formed essentially entirely from the elastomeric component and the remaining fibers are formed essentially entirely from the plastic component. Polymeric materials can also include combinations of the foregoing (e.g., plastoelastic blend fibers and bicomponent fibers, plastoelastic blend fibers and mixed fibers, bicomponent fibers and mixed fibers). A further example of a plastoelastic material is a plastoelastic blend in the form of a heterogeneous mixture having a co-continuous morphology with both phases forming interpenetrating networks.

Suitable examples of plastoelastic materials include the elastomeric component in a range of about 5 wt. % to about 95 wt. % and from about 40 wt. % to about 90 wt. %, based on the total weight of the plastoelastic material. Suitable examples of the plastoelastic materials include the plastic component in a range of about 5 wt. % to about 95 wt. %, and from about 10 wt. % to about 60 wt. %, based on the total weight of the plastoelastic material. When the plastoelastic material includes mixed elastic and plastic fibers, the elastic fibers may be included in an amount from about 40 wt. % to about 60 wt. %, for example about 50 wt. % (with the approximate balance being the plastic fibers), based on the total weight of the mixed elastic and plastic fibers. When the plastoelastic material includes bi-component fibers, the plastic component (e.g., in the form of a sheath) may be included in an amount of about 20 wt. % or less or about 15 wt. % or less, for example about 5 wt. % to about 10 wt. % (with the approximate balance being the elastic component, for example as a fiber core), based on the total weight of the bi-component fibers. When the plastoelastic material includes a plastoelastic blend, the elastic component may be included in an amount from about 60 wt. % to about 80 wt. %, for example about 70 wt. % (with the approximate balance being the plastic component), based on the total weight of the plastoelastic blend. In some embodiments, the plastoelastic material can include more than one elastomeric component and/or more than one plastic component, in which case the stated concentration ranges apply to the sum of the appropriate components and each component may be incorporated at a level of at least about 5 wt. %.

The elastomeric component may provide the desired amount and force of recovery upon the relaxation of an elongating tension on the plastoelastic material, especially upon strain cycles following the initial shaping strain cycle. Many elastic materials are known in the art, including synthetic or natural rubbers (e.g., crosslinked polyisoprene, polybutadiene and their saturated versions (after hydrogenation), and polyisobutylene), thermoplastic elastomers based on multiblock copolymers, such as those comprising copolymerized rubber elastomeric blocks with polystyrene blocks (e.g., styrene-isoprene-styrene, styrene-butadiene-styrene, styrene-ethylene/butylene-styrene, styrene-ethylene/propylene-styrene, and styrene-butadiene/isoprene-styrene, including their hydrogenated and non-hydrogenated forms), thermoplastic elastomers based on polyurethanes (which form a hard phase that provides high mechanical integrity when dispersed in an elastomeric phase by anchoring the polymer chains together), polyesters, polyether amides, elastomeric polyethylenes, elastomeric polypropylenes, and combinations thereof. Some particularly suitable examples of elastic components include styrenic block copolymers, elastomeric polyolefins, and polyurethanes.

Other particularly suitable examples of elastic components include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518,378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher α-olefin) incorporated into the backbone. Suitable elastomeric RCP materials are available under the names VISTAMAXX (available from ExxonMobil, Houston, Tex.) and VERSIFY (available from Dow Chemical, Midland, Mich.).

When the BSOC includes a printed elastic material, the elastomeric component may be a styrenic block copolymer.

Other commercially available polymers suitable as the elastomeric component include KRATON (styrenic block copolymer; available from the Shell Chemical Company, Houston, Tex.), SEPTON (styrenic block copolymer; available from Kuraray America, Inc., New York, N.Y.), VECTOR (styrenic block copolymer; available from Dexco Chemical Company, Houston, Tex.), ESTANE (polyurethane; available from Noveon, Inc., Cleveland, Ohio), PEBAX (polyether amide; available from Atofina Chemicals, Philadelphia, Pa.), and HYTREL (polyester; available from DuPont, Wilmington, Del.).

The plastic component of the plastoelastic material may provide the desired amount of permanent plastic deformation imparted to the material during the initial shaping strain cycle, whether included in a plastoelastic blend or in a discrete plastic component. Typically, the higher the concentration of a plastic component in the plastoelastic material, the greater the possible permanent set following relaxation of an initial straining force on the material. Suitable plastic components generally include higher crystallinity polyolefins that are plastically deformable when subjected to a tensile force in one or more directions, for example high density polyethylene, linear low density polyethylene, very low density polyethylene, a polypropylene homopolymer, a plastic random poly(propylene/olefin) copolymer, syndiotactic polypropylene, polybutene, an impact copolymer, a polyolefin wax, and combinations thereof. Another suitable plastic component is a polyolefin wax, including microcrystalline waxes, low molecular weight polyethylene waxes, and polypropylene waxes. Suitable materials include LL6201 (linear low density polyethylene; available from ExxonMobil, Houston, Tex.), PARVAN 1580 (low molecular weight polyethylene wax; available from ExxonMobil, Houston, Tex.), MULTIWAX W-835 (microcrystalline wax; available from Crompton Corporation, Middlebury, Conn.); Refined Wax 128 (low melting refined petroleum wax; available from Chevron Texaco Global Lubricants, San Ramon, Calif.), A-C 617 and A-C 735 (low molecular weight polyethylene waxes; available from Honeywell Specialty Wax and Additives, Morristown, N.J.), and LICOWAX PP230 (low molecular weight polypropylene wax; available from Clariant, Pigments & Additives Division, Coventry, R.I.).

Other polymers suitable as the plastic component, whether included in the nonwoven fibers or the polymeric layer, are not particularly limited as long as they have plastic deformation properties. Suitable plastic polymers include polyolefins generally, polyethylene, linear low density polyethylene, polypropylene, ethylene vinyl acetate, ethylene ethyl acrylate, ethylene acrylic acid, ethylene methyl acrylate, ethylene butyl acrylate, polyurethane, poly(ether-ester) block copolymers, poly(amide-ether) block copolymers, and combinations thereof. Suitable polyolefins generally include those supplied from ExxonMobil (Houston, Tex.), Dow Chemical (Midland, Mich.), Basell Polyolefins (Elkton, Md.), and Mitsui USA (New York, N.Y.). Suitable plastic polyethylene films are available from RKW US, Inc. (Rome, Ga.) and from Cloplay Plastic Products (Mason, Ohio).

Fibrous Materials

The nonwoven fibrous material of the present invention is generally formed from fibers which are interlaid in an irregular fashion using such processes as meltblowing, spunbonding, spunbonding-meltblowing-spunbonding (SMS), air laying, coforming, and carding. The nonwoven material may include spunbond fibers. The fibers of the nonwoven material may be bonded together using conventional techniques, such as thermal point bonding, ultrasonic point bonding, adhesive pattern bonding, and adhesive spray bonding. The basis weight of the resulting nonwoven material can be as high as about 100 g/m$^2$ (grams per square meter), but may also be less than about 80 g/m$^2$, less than about 60 g/m$^2$, and even less than about 50 g/m$^2$, for example less than about 40 g/m$^2$. Unless otherwise noted, basis weights disclosed herein are determined using European Disposables and Nonwovens Association ("EDANA") method 40.3-90.

In one example of an embodiment of the present invention, the nonwoven material can include two or, optionally, three different layers of fibers: a first layer of nonwoven fibers having a first number-average fiber diameter, a second layer of fibers having a second number-average fiber diameter that is smaller than the first number-average fiber diameter, and optionally a third layer of fibers having a third number-average fiber diameter that is smaller than the second number-average fiber diameter. The ratio of the first diameter to the second diameter is generally about 2 to about 50, or about 3 to about 10, for example about 5. The ratio of the second diameter to the third diameter is generally about 2 to about 10, for example about 5. In this embodiment, the second layer of fibers is disposed on the first layer of nonwoven fibers, and the third layer of fibers (when included) is disposed on the second layer of fibers. This arrangement can include the case where the first and second (and optionally third) fiber layers form essentially adjacent layers such that a portion of the layers overlap to form an interpenetrating fiber network at the interface (e.g., fibers from the first and second layers overlap and/or fibers from the second and third layers overlap). This arrangement can also include the case where the first and second fiber layers are essentially completely intermingled to form a single heterogeneous layer of interpenetrating fibers.

In this example of an embodiment, the first number-average fiber diameter may be in a range of about 10 μm to about 30 μm, for example about 15 μm to about 25 μm. Suitable fibers for the first group of nonwoven fibers include spunbond fibers. The spunbond fibers can include the various combinations of elastomeric and plastic components described above.

In this example of an embodiment, the second number-average fiber diameter may be in a range of about 1 μm to about 10 μm, for example about 1 μm to about 5 μm. Suitable fibers for the second group of fibers include meltblown fibers, which can be incorporated into the nonwoven material in one or more layers. The meltblown fibers may have a basis weight in a range of about 1 g/m$^2$ to about 20 g/m$^2$ or about 4 g/m$^2$ to about 15 g/m$^2$, distributed among the various meltblown layers. The meltblown fibers can include the various combinations of elastomeric and plastic components described above, and may also include elastic materials and/or plastoelastic materials. A higher elastomeric content may be preferred when higher depths of activation are required and/or when lower permanent set values in the outer cover are desired. Elastomeric and plastic polyolefin combinations can be utilized to optimize the cost/performance balance. In some embodiments, the elastomeric component can include a very low crystallinity polypropylene (e.g., VISTAMAXX polypropylene available from ExxonMobil, Houston, Tex.).

Figure 2:
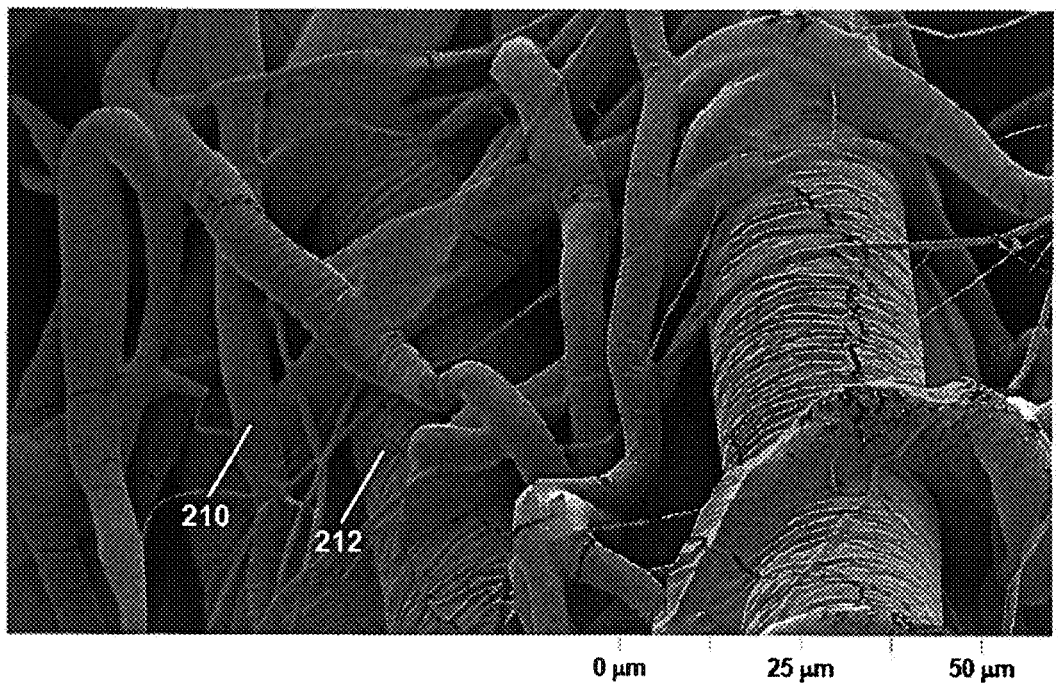
FIG. 2 is a scanning electron micrograph of the spunbond-meltblown-spunbond nonwoven material of FIG. 1 after mechanical activation.

The fine fibers of the meltblown layer may enhance the opacity of the BSOC, which is typically a desirable feature in outer covers. The meltblown fibers may also have the beneficial effect of improving the structural integrity of the nonwoven material when the meltblown fibers overlap and are dispersed among the other nonwoven fibers of the nonwoven material, for example in an SMS nonwoven laminate in which the meltblown layer is disposed between and joined to two spunbond layers. The microstructure of an SMS nonwoven laminate is shown in the scanning electron micrographs ("SEMs") of FIG. 1 (before mechanical activation) and FIG. 2 (after mechanical activation). The figures illustrate that finer (meltblown) fibers 210 are intertwined with coarser (spunbond) fibers 212. The self-entanglement resulting from the incorporation of fibers having substantially different length scales can increase the internal adhesive integrity of the nonwoven material, thereby lessening (and potentially even eliminating) the need for the bonding of the nonwoven material. The meltblown fibers can also form a "tie-layer" increasing the adhesion between the other nonwoven fibers and an adjacent polymeric layer, in particular when the meltblown fibers are formed from an adhesive material. The presence of the meltblown fibers can also have the beneficial effect of reducing the post-activation % set by a relative amount of at least about 5% (i.e., relative to a nonwoven material that is otherwise the same except for the meltblown fibers) or at least about 8%, for example at least about 10%. FIG. 2 illustrates that the intertwined structure formed when the fibers are first laid (i.e., as shown in FIG. 1) remains intact after the mechanical activation process.

Figure 3:
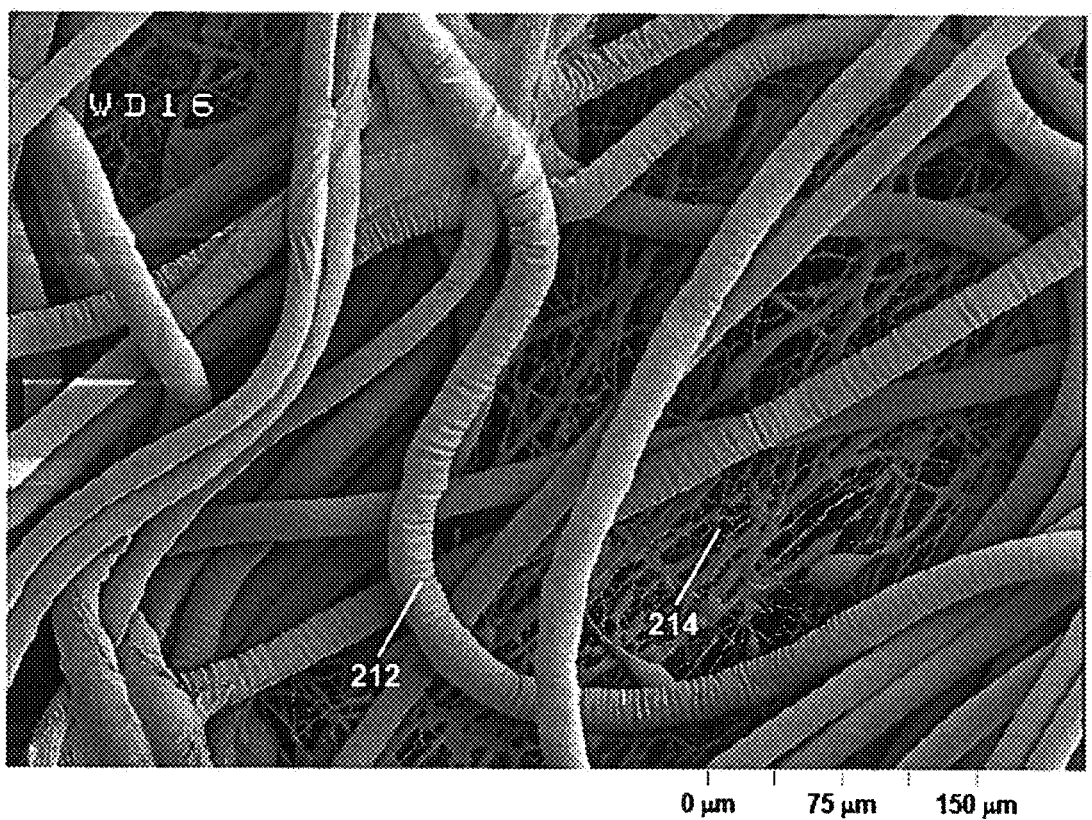
FIG. 3 is a scanning electron micrograph of a spunbond-nanofiber-spunbond nonwoven material prior to mechanical activation.

The second number-average fiber diameter may alternatively or additionally be in a range of about 0.1 μm to about 1 μm, for example about 0.5 μm. Suitable fibers for such a second group of fibers include nanofibers, which can have the compositions described above for meltblown fibers. Using nanofibers either in place of meltblown fibers (in which case the nanofibers form the second layer of fibers) or in addition to meltblown fibers (in which case the nanofibers form the third layer of fibers) can further increase the opacity of the outer cover, and can also provide the structural and adhesive advantages mentioned above in relation to meltblown fibers. FIG. 3 illustrates a layer of finer nanofibers 214 below a layer of coarser spunbond fibers 212 in an SEM of a spunbond-nanofiber-spunbond ("SNS") laminate. From FIG. 3, it is apparent that the void surface areas resulting in the upper spunbond layer are substantially filled by the underlying nanofiber layer, thereby improving the opacity. When they are included, the nanofibers may have a basis weight in a range of about 1 g/m$^2$ to about 7 g/m$^2$, for example in a range of about 3 g/m$^2$ to about 5 g/m$^2$. At such levels, the nanofibers can provide a relative increase (i.e., relative to a nonwoven material that is otherwise the same except for the nanofibers) in the opacity of the nonwoven material of at least about 5%, or at least about 8%, for example at least about 10%. In an alternate embodiment, opacifying particles such as titanium dioxide can be included in the nanofibers to further increase the opacity.

Figure 10:
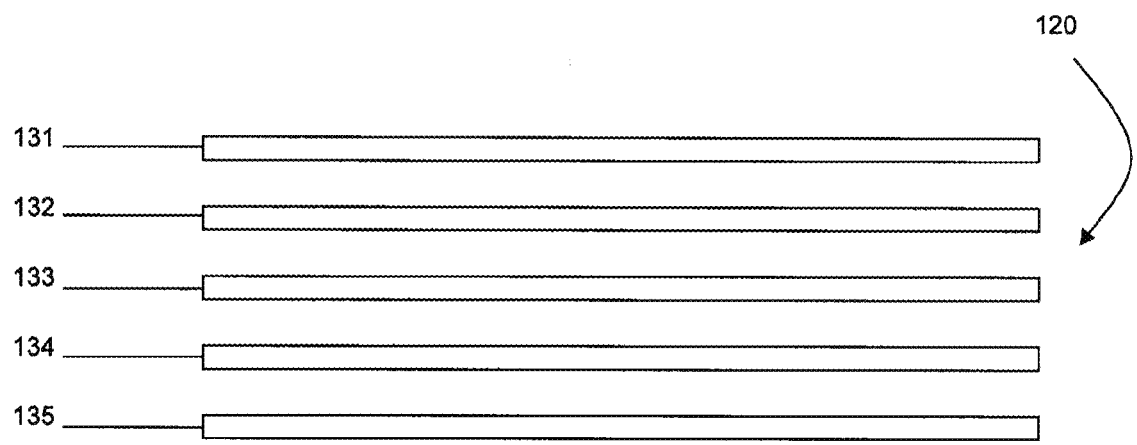
FIG. 10 is sectional side view of a multilayered nonwoven material.

FIG. 10 shows another example of an embodiment of the present invention. The nonwoven material 120 may include at least four, and optionally five, layers of fibers of differing kinds in a stacked arrangement. The first (top) layer 131 may include spunbond fibers such as, for example, mixed elastomeric fibers and plastic fibers, bi-component elastomeric and plastic fibers, and plastoelastic blend fibers, which include elastomeric polypropylene. The second layer 132 may be disposed on the first layer 131 and can include meltblown fibers such as, for example, elastomeric fibers that include but are not limited to elastomeric polypropylene or elastomeric polyethylene. The third layer 133 may be disposed on the second layer 132 and can include nanofibers that are generally either elastomeric fibers (for example including either elastomeric polypropylene or elastomeric polyethylene) or plastoelastic blend fibers (for example including elastomeric polypropylene). The fourth layer 134 may be disposed on the third layer 133 and can include meltblown fibers such as, for example, plastoelastic blend fibers including elastomeric polypropylene. Other possible materials for the first through fourth layers 131, 132, 133, and 134 are the same as those described above under "Polymeric Materials."

The optional fifth (bottom) layer 135 may be joined to the fourth layer 134 and can include spunbond (or, alternatively, carded) fibers that are generally either plastic fibers (for example including high-extensibility nonwoven fibers or a high-elongation carded web material) or plastoelastic blend fibers. When the fifth layer 135 includes plastic fibers, it may be advantageous to provide plastic fibers that are extensible enough to survive the mechanical activation process. Suitable examples of such sufficiently deformable spunbond fibers are disclosed in WO 2005/073308 and WO 2005/073309. Suitable commercial plastic fibers for the fifth layer 135 include a deep-activation polypropylene, a high-extensibility polyethylene, and polyethylene/poly-propylene bi-component fibers (all available from BBA Fiberweb Inc., Simpsonville, S.C.). The fifth layer 135 can be added to the nonwoven material at the same time as the first four layers 131, 132, 133, and 134, or the fifth layer 135 can be added later in a production process for an absorbent article. Adding the fifth layer 135 later in the production process permits greater BSOC flexibility, for example allowing the intercalation of absorbent article components (e.g., a high-performance elastomeric band) into the BSOC and permitting the omission of the fifth layer 135 in regions where it is not required in the absorbent article (e.g., where the BSOC is positioned on the absorbent core).

In various embodiments of the present invention, the coarse spunbond fibers may provide the desirable mechanical properties of the resulting material, the fine meltblown fibers may increase the opacity and the internal adhesive integrity of the resulting material, and the even finer nanofibers may further increase the opacity. Each spunbond or carded layer may be included in the nonwoven material at a basis weight of at least about 10 g/m$^2$, for example at least about 13 g/m$^2$ and may be included in the nonwoven material at a basis weight preferably of about 50 g/m$^2$ or less, for example about 30 g/m$^2$ or less. Each meltblown and nanofiber layer may be included in the nonwoven material at a basis weight of at least about 1 g/m$^2$, for example at least about 3 g/m$^2$ and may be included in the nonwoven material at a basis weight of about 7 g/m$^2$ or less, for example about 5 g/m$^2$ or less. The final nonwoven material has a basis weight in a range of about 25 g/m$^2$ to about 100 g/m$^2$, for example about 35 g/m$^2$ to about 80 g/m$^2$. The final outer cover can also include a laminated polymeric film or a printed elastic layer of the kinds described below.

For BSOCs including an elastomeric film and plastic nonwovens, pin holing can be a potential issue during mechanical activation, especially at high speeds. In some embodiments of the present invention it is critical to prevent pinholing during activation. Extensible nonwovens may help mitigate or even resolve this issue. A key property that characterizes an extensible nonwoven is its peak elongation (i.e., the higher the peak elongation, the more extensible the nonwoven). Tearing of the BSOC may result during mechanical activation when including conventional plastic nonwovens in the BSOC. On the other hand, plastic nonwovens that have peak elongations greater than about 100%, greater than about 120%, or even greater than about 150%, for example 180% may reduce the likelihood of tearing the BSOC during mechanical activation.

One suitable example of such an extensible nonwoven is Softspan 200 made by BBA (Fiberweb), Simpsonville, S.C., which has a peak elongation of about 200%.

Laminated Polymeric Films and Printed Elastic Layers

The polymeric film of the present invention can be formed with conventional equipment and processes, such as, for example using cast film or blown film equipment. The polymeric film also can be coextruded with the nonwoven fibers. The polymeric film also can be colored, for example by adding a dye to the resin before the film is formed (which method of coloration can also be used for the polymeric fibrous materials of the invention). The basis weight of the resulting polymeric film may in a range of about 10 g/m$^2$ to 40 g/m$^2$ or in a range of about 12 g/m$^2$ to 30 g/m$^2$, for example in a range of about 15 g/m$^2$ to 25 g/m$^2$. The polymeric film may have a thickness of less than about 100 μm or the polymeric film may have a thickness of about 10 μm to 50 μm.

In an embodiment, the polymeric film can be formed from multiple layers coextruded into a single multi-layer film. A multi-layer film may permit tailoring the properties of the film to the specific needs of the application by decoupling the bulk and surface properties in the final film. For instance, antiblock additives can be confined to the skin layers (i.e., an exterior layer in the final film). Alternatively, a higher crystallinity, higher melting-point elastomeric component (e.g., VM3000 film-grade VISTAMAXX, having a first melting temperature $T_{m,1}$>60° C., instead of VM1100 film-grade VISTAMAXX, having a first melting temperature $T_{m,1}$~50° C.) can be used in the skin layer to reduce tackiness. A plastoelastic skin layer can similarly reduce tackiness. Both tackiness-reduction options can enhance the thermal stability of the final film and increase its toughness, thereby preventing tear initiation and/or propagation in apertured films and laminates. The core layer (i.e., an interior layer in the final film) can include blends of elastomeric polypropylene and a styrenic block copolymer. Alternatively or additionally, both the core and skin layers can contain sufficient amounts of filler particles to become microporous upon activation (thereby increasing the breathability of the film), yet they can have different base polymeric components. Three examples of suitable multi-layer films include: (1) a lower melting point elastomeric polypropylene core laminated with a higher melting point elastomeric polypropylene skin, (2) a lower melting point blended core of elastomeric polypropylene and a styrenic block copolymer laminated with a higher melting point elastomeric polypropylene skin, and (3) a filled blended core of a plastoelastic polymer and a styrenic block copolymer laminated with a filled plastic polyethylene skin.

When the BSOC includes a printed elastic material, the elastomeric component can be printed onto the plastic layer of nonwoven fibers using conventional printing techniques. Non-limiting examples of such printing techniques include intaglio printing (gravure and offset gravure), relief printing (flexographic and letterpress), planographic printing, ink jet printing and the like. Each of these printing methods may provide a wide range of deposition amounts of an elastomeric component in various shapes and directions, which in turn can provide design flexibility, which may ultimately result in an improved fit for an absorbent article formed with the BSOC of the present disclosure. Suitable examples of elastomer printing processes are disclosed in: U.S. Pat. No. 7,056,411, filed on Nov. 5, 2002, issued to Desai, et al., US Patent Publication No. 20030088228, filed on Nov. 5, 2002, by Desai, et al., US Patent Publication No. 2004/0193133, filed on Mar. 29, 2004 by Desai, et al., US Patent Publication No. 20040222553, filed May 5, 2003 by Desai, et al., US Patent Publication No. 20050214461, filed on Mar. 16, 2005 by Desai, et al., International Publication No. WO 2005/097358, filed on Mar. 24, 2005 by Desai et al., International Publication No. WO 2005/097512, filed on Mar. 24, 2005 by Desai et al. The printing processes may also include the application of a color, such as, for example via a dye or pigment, to at least one of the outer cover components.

The elastomeric component can be printed onto the plastic layer of nonwoven fibers as a continuous film or as a pattern. If printed as a pattern, the pattern can be relatively regular, covering substantially the entire area of the outer cover, for example, in a continuous mesh pattern or a discontinuous dot pattern. The pattern can also include regions of relatively higher or lower basis weights wherein the elastomeric component has been applied onto at least one region of the plastic layer of nonwoven fibers to provide particular stretch properties to a targeted region of the BSOC (i.e., after biaxial mechanical activation).

The polymeric film can optionally include organic and inorganic filler particles. The filler particles may be small (e.g., about 0.4 µm to about 8 µm average diameter) to produce micropores that are sufficient to simultaneously promote the breathability of the film and maintain the liquid water barrier properties of the film. Suitable fillers include calcium carbonate, non-swellable clays, silica, alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, glass particles, pulp powder, wood powder, chitin, chitin derivatives, and polymer particles. A suitable inorganic filler particle for improving the breathability of the film is calcium carbonate. Suitable organic filler particles include submicron (e.g., about 0.4 µm to about 1 µm) polyolefin crystals that are formed by the crystallization of the low crystallinity random copolymers. Such organic filler particles may be highly covalently connected to the non-crystalline elastomeric regions of the film, and thus may be effective at reinforcing the film, in particular polyethylene- and polypropylene-based systems. Some filler particles (e.g., titanium dioxide) may also serve as opacifiers (i.e., they improve the opacity of the polymeric film) when incorporated at relatively low levels (e.g., about 1 wt. % to about 5 wt. %). The filler particles can be coated with a fatty acid (e.g., up to about 2 wt. % of stearic acid or a larger chain fatty acid such as behenic acid) to assist dispersion into the polymeric film. The polymeric film may include about 30 wt. % to about 70 wt. % of the filler particles, for example including about 40 wt. % to about 60 wt. % filler particles, based on the total weight of the filler particles and the polymeric film.

A method that may improve the breathability of the polymeric film includes the use of discontinuous and/or apertured films. Known methods for creating small apertures either throughout the entire surface area of the film or in discrete regions of the film (e.g., the side panel areas and/or the waistband of an absorbent article) include, for example, mechanical punching or hot-pin aperturing. It is to be understood, however, that any suitable method for creating apertures in a film commonly known to those of ordinary skill in the art is contemplated by the present invention. The total area formed by the apertures may be between about 2 and about 20% of the total film surface area, based on trade-offs between breathability, opacity, and load/unload profiles. Pattern selection is largely dictated by the need to minimize stress concentration around the apertures to mitigate the risk of tearing during mechanical activation. Because of the nature of the formulations, the apertures introduced into the film may initially be very small or be in the form of tiny defects which then expand into larger apertures as the polymeric film is stretched. The apertures can be created as part of the film-making process via a vacuum-forming process or a high pressure jet which produces three-dimensional cone-shaped structures around the apertures that help alleviate the risk of tear initiation and propagation during subsequent activation.

Final Processing of the BSOC

In embodiments containing the polymeric film, the nonwoven material and the polymeric film may be laminated together with the machine directions of each substantially aligned with the other. The bonding may be accomplished using conventional techniques such as adhesive lamination, extrusion lamination, thermal point bonding, ultrasonic point bonding, adhesive pattern bonding, adhesive spray bonding, and other techniques maintaining the breathability of the film (e.g., those where the bonded areas cover less than about 25% of the interface between the polymeric film and nonwoven fibers). The nonwoven material may be partially activated prior to laminate formation. Partial activation of the nonwoven material may reduce the risk of pinhole formation in the film, and thus may facilitate the activation process on the final nonwoven-film laminate.

Figure 11:
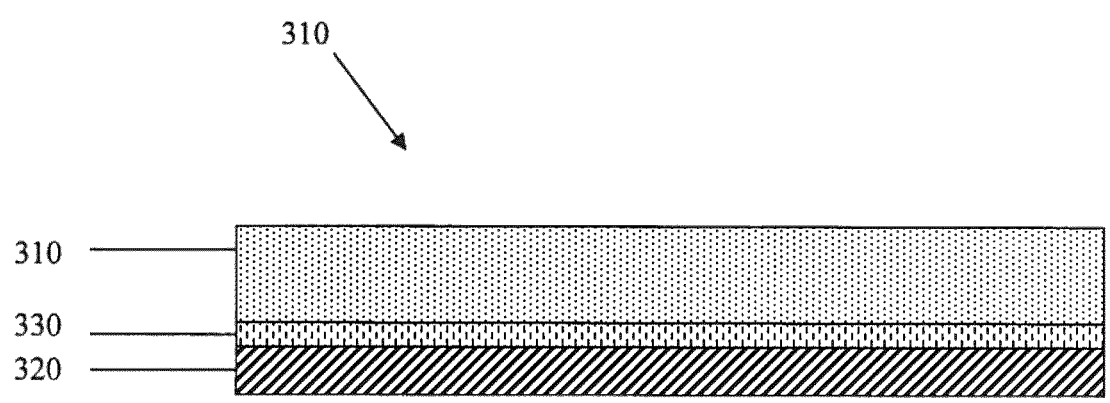
FIG. 11 is sectional side view of a biaxially stretchable outer cover.

FIG. 11 shows an example of a BSOC 300 that includes a nonwoven material 310 joined to a polymeric film material 320. The nonwoven material 310 may be joined to the film material 320 by an adhesive 330. The nonwoven 310 and film 320 materials and configurations may include any suitable material or configuration desired such as, for example, one or more of the materials or configurations described herein. Additionally, the nonwoven 310 and film 320 materials may be joined by any suitable means described herein or commonly known in the art, as desired.

In an alternate embodiment, a fibrous meltblown layer of adhesive may be applied to create the nonwoven-film laminate. Elastomeric polyolefin glue is a nonlimiting example of a suitable adhesive. Other suitable adhesives commonly known in the art, such as, for example styrenic block copolymers, may also be used. This can reduce the amount of adhesive used to create the laminate because of the mechanical adhesive effect of entangling meltblown fibers with spunbond fibers as discussed above and shown in FIGS. 1 and 2.

In another embodiment, a polymeric film can be included between the various nonwoven fiber layers instead of the polymeric film that is laminated to the outer layer of the nonwoven material (i.e., the composite material formed by the individual distinct nonwoven fiber layers). This polymeric film may be a polyethylene-based film (which is rendered breathable after activation) that even more preferably contains opacifying particles and/or filler particles. In one embodiment, the five-layer nonwoven structure discussed above (i.e., the spunbond-meltblown-nanofiber-meltblown-spunbond or "SMNMS") may be modified such that the nanofiber layer is replaced with this polymeric film. This polymeric film can be either adhesively laminated or extrusion-laminated to the adjacent nonwoven fibers. The laminate structure of this embodiment provides the adhesive and structural benefits of the meltblown layers discussed above and also prevents pinhole formation in the interior polymeric film (because of the protection afforded by the meltblown buffer layers).

In another embodiment, a portion of the BSOC (e.g., a first spunbond layer and, optionally, a second meltblown layer; a polymeric film) may be pre-stretched in either or both the MD and the CD immediately after being laid and just prior to the addition of more layers to the material. Pre-stretching in the MD can be accomplished by accelerating the web through a set of process rolls. Pre-stretching in the CD can be performed in the same manner as in a tenterframing process, or by using a set of rolls with diverging hills and valleys that force the material outward. Additional BSOC layers (i.e., fibrous layers or film layers) may then be added onto the pre-stretched material before being subjected to thermal bonding. The resultant material requires less mechanical activation to exhibit stretch/recovery at any given strain, and it can also minimize the amount of necking during a stretch operation (i.e., size reduction in CD resulting from pulling in the MD). This embodiment may be useful in depositing larger amounts of the additional component per surface area of the nonwoven material in its relaxed state. Pre-stretching can also reduce pinhole formation in the polymeric film in a subsequent activation process.

The outer cover material can be rendered stretchable using a mechanical activation process in both the machine and/or cross machine directions. Such processes typically increase the strain range over which the web exhibits stretch/recovery properties and impart desirable tactile/aesthetic properties to the material (e.g., a cotton-like texture). Mechanical activation processes include ring-rolling, SELFing (differential or profiled), and other means of incrementally stretching webs as known in the art. An example of a suitable mechanical activation process is the ring-rolling process, described in U.S. Pat. No. 5,366,782. Specifically, a ring-rolling apparatus includes opposing rolls having intermeshing teeth that incrementally stretch and thereby plastically deform the material (or a portion thereof) forming the outer cover, thereby rendering the outer cover stretchable in the ring-rolled regions. Activation performed in a single direction (for example the cross direction) yields an outer cover that is uniaxially stretchable. Activation performed in two directions (for example the machine and cross directions or any two other directions maintaining symmetry around the outer cover centerline) yields an outer cover that is biaxially stretchable. In some embodiments, the BSOC is activated in at least one region (e.g., a portion of at least one of the front or back waist regions) and remains unactivated in at least one other region, which other region can include a structured elastic-like formed web material.

In some embodiments, the BSOC is intentionally activated to differing degrees in different regions (including completely unactivated regions). This manner of processing allows certain regions of the BSOC to be elongated to variable extents, thereby permitting the processing of more complex shapes (which in turn reduces the need to trim the BSOC into a desired shape). Additionally, a BSOC containing unactivated regions can be incorporated into an absorbent article. This permits the consumer to manually stretch the absorbent article (e.g., a diaper), thereby inducing some permanent plastic deformation (i.e., the consumer manually activates the absorbent article) in a manner that provides an improved fit of the absorbent article for the wearer. When the consumer manually activates the absorbent article, absorbent articles manufactured in a single size can comfortably accommodate a wider size range of consumers.

Physical Properties of the BSOC

The usefulness of a BSOC according to the present invention relates to a variety of physical properties. The mechanical properties of the BSOC relate, for instance, to the ability of the outer cover to survive the high-strain-rate activation process and the ability of an absorbent article incorporating a BSOC to conform to a wearer's body in a way that prevents leaks, improves fit, and improves comfort. Aesthetic properties such as opacity and texture (e.g., a cotton, ribbon-like texture) affect consumer appeal for the final absorbent article product. Other physical properties such as breathability and liquid permeability affect comfort of the absorbent article product wearer.

The tensile strain (%) at breaking and % set are relevant mechanical properties. The tensile strain at breaking may be in a range of about 200% to about 600%, or in a range of about 220% to about 500%, for example in a range of about 250% to about 400%. The tensile strain at breaking relates to the ability of the BSOC to withstand the activation process and to react to stresses during normal use. The % set of the BSOC can be as high as 70% when subjected to a pre-activation hysteresis test, and such % set values may allow the BSOC simultaneously to be down-gauged (i.e., into a thinner material with a lower basis weight) and/or formed into complex planar or three-dimensional shapes during the activation process. After activation with a strain of about 175% (for example with a pair of flat ring-roll plates having a depth of engagement of about 2.6 mm and a pitch of about 2.5 mm), the first cycle % set of the BSOC may be about 20% or less or about 15% or less, for example about 10% or less when subjected a hysteresis test having only a 75% strain first loading cycle and a 75% strain second loading cycle. Similarly, prior to any form of activation, the first cycle % set of the BSOC may be about 20% or less or about 15% or less, for example about 10% or less when subjected a hysteresis test having a 200% strain prestrain loading cycle, a 50% strain first loading cycle, and a 50% strain second loading cycle. The low first cycle % set values (whether post-activation or whether after a prestrain loading cycle that simulates the effect of activation) relate to the ability of the BSOC to elastically conform to a wearer's body during use, thereby potentially providing a comfortable and leak-resistant absorbent article.

A high opacity is a desirable aesthetic property of the BSOC, because it provides the consumer with the impression that the BSOC will have favorable liquid-retention properties. The opacity of the BSOC is preferably at least about 65%, more preferably at least about 70%, for example at least about 75%, in particular when the BSOC does not include the polymeric layer.

Even though the absorbent core of an absorbent article may include a containment member to limit the escape of liquids, the BSOC is typically at least partially liquid-impermeable to serve as an additional means for containing waste liquids. Thus, the BSOC may be liquid-impermeable to the extent that it has a hydrostatic head ("hydrohead") pressure up to about 80 mbar or about 7 mbar to about 60 mbar, for example about 10 mbar to about 40 mbar.

The breathability of a BSOC relates to its ability to allow moisture vapor (e.g., water vapor from waste liquid contained in the absorbent core) to permeate the BSOC and exit an absorbent article, thereby keeping the wearer's skin dry and free from irritation. The breathability of a BSOC is characterized by its moisture vapor transmission rate ("MVTR"). The MVTR of a BSOC that includes only nonwoven material and does not include a polymeric film is not particularly limited, and is preferably at least about 6,000 g/m$^2$ day, with values of at least about 9,000 g/m$^2$ day being relatively easily attainable. When the BSOC includes the polymeric film, which film tends to inhibit vapor transmission, the film often includes filler particles and/or is processed to form apertures so that breathability is improved. For BSOCs including the film, the MVTR may be about 1,000 g/m$^2$ day to about 10,000 g/m$^2$ day, or about 1,000 g/m$^2$ day to about 6,000 g/m$^2$ day, for example about 1,200 g/m$^2$ day to about 4,000 g/m$^2$ day.

Application

Inclusion of a BSOC in an Absorbent Article

Figure 4:
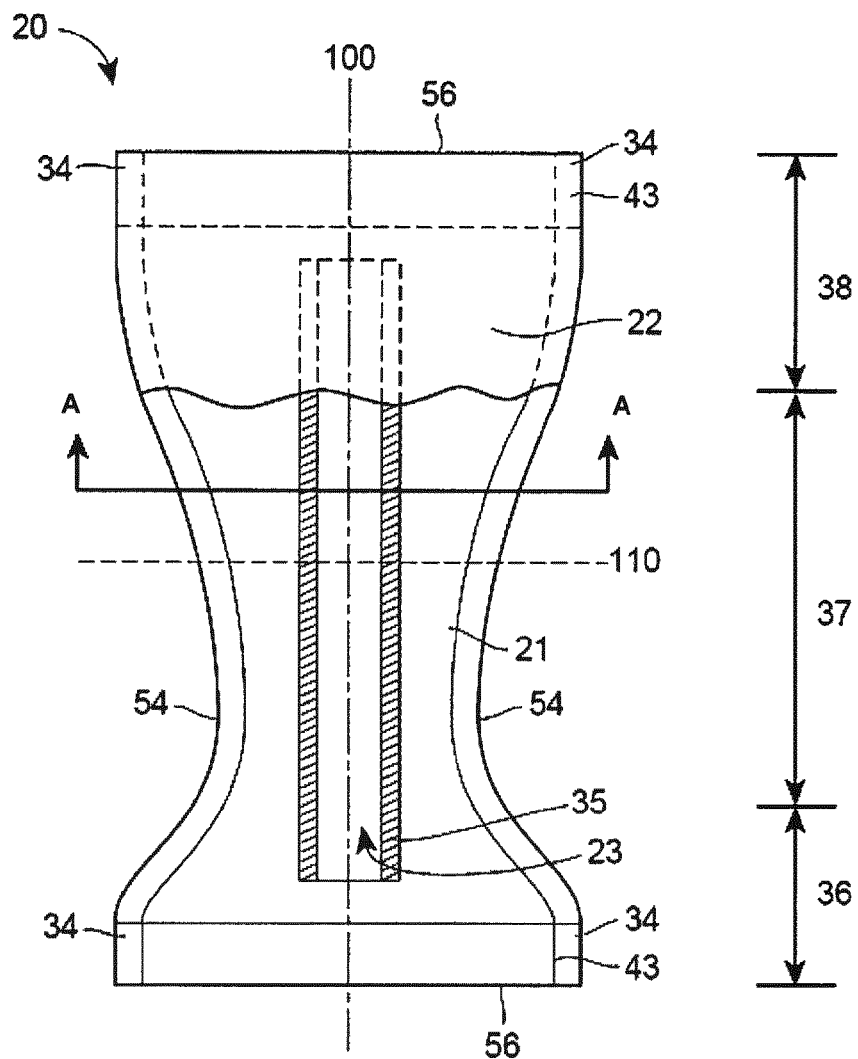
FIG. 4 is a top plan view of an absorbent article including a BSOC.
Figure 5:
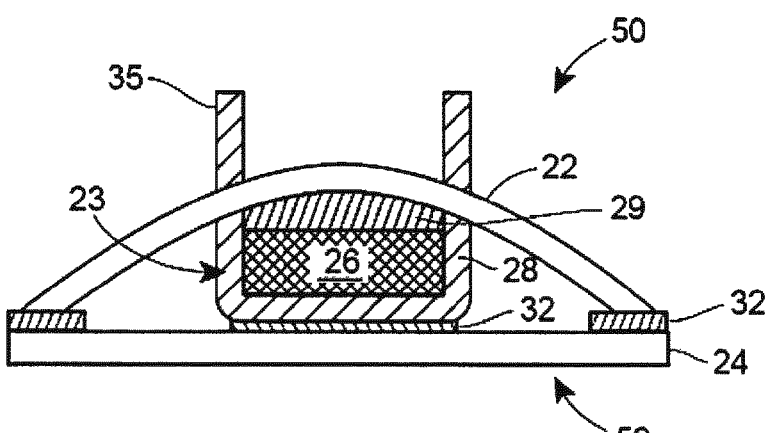
FIG. 5 is a sectional side view of an example of the absorbent article of FIG. 4 along line A-A.
Figure 5A:
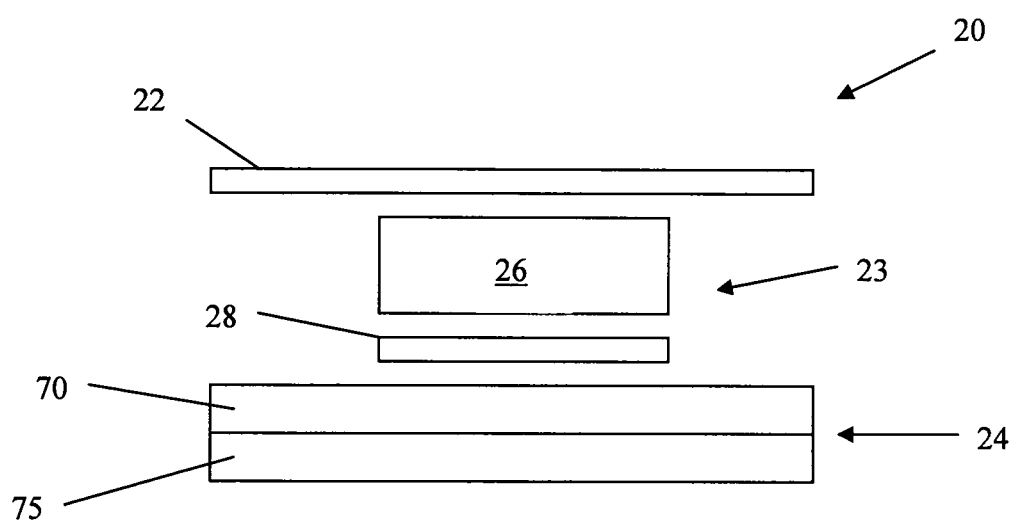
FIG. 5A is a sectional side view of an example of the absorbent article of FIG. 4 along line A-A.

FIGS. 4, 5 and 5A show an absorbent article (illustrated as a pant-like diaper 20) constructed in accordance with the present invention. The diaper 20 has a longitudinal centerline 100 and a lateral centerline 110. The diaper 20 defines an inner surface 50 and an opposing outer surface 52. The inner surface 50 generally includes that portion of the diaper 20 which is positioned adjacent the wearer's body during use (i.e., the wearer-facing side), while the outer surface 52 generally comprises that portion of the diaper 20 which is positioned away from the wearer's body (i.e., the garment-facing side).

The diaper 20, includes a chassis 21 having a first, or front, waist region 36, a second, or back, waist region 38 opposed to the front waist region 36, and a crotch region 37 located between the front waist region 36 and the back waist region 38. The waist regions 36 and 38 generally include those portions of the diaper 20 which, when the diaper 20 worn, encircle the waist of the wearer. The waist regions 36 and 38 can include elastic elements such that they gather about the waist of the wearer to provide improved fit and containment. The crotch region 37 is that portion of the diaper 20 which, when the diaper 20 is worn, is generally positioned between the legs of the wearer.

The outer periphery of the chassis 21 is defined by lateral end edges 56 that can be oriented generally parallel to the lateral centerline 110, and by longitudinal side edges 54 that can be oriented generally parallel to the longitudinal centerline 100 or, for better fit, can be curved or angled, as illustrated, to produce an "hourglass" shaped garment when viewed in a plan view. In some embodiments, the longitudinal centerline 100 can bisect the end edges 56 while the lateral centerline 110 can bisect the side edges 54.

The chassis 21 of the diaper 20 generally includes a liquid-permeable topsheet 22, a liquid-impermeable BSOC 24, and an absorbent core assembly 23 disposed between the topsheet 22 and the BSOC 24. The BSOC 24 can be any of the outer covers having biaxial stretch properties and/or configurations disclosed herein such as, for example, the configurations shown in FIGS. 10 and/or 11. Specifically, any of the disclosed BSOCs including plastoelastic materials and/or discrete elastic materials in combination with discrete plastic materials are suitable. One example, shown in FIG. 5A, is a diaper 20 having a BSOC 24 formed from a first fiber layer 70 and a second fiber layer 75 disposed on the first fiber layer 70. In this example, the diaper 20 includes a topsheet 22 and a core assembly 23 disposed between the topsheet 22 and the BSOC 24. The core assembly 23 includes an absorbent core 26 and a containment member 28, which is described in more detail below.

The core assembly 23 can be positioned on a wearer-facing surface of the outer cover 24. The core assembly 23 can be attached to the BSOC 24 via any suitable adhesive or cohesive 32 (as illustrated) or via any other suitable means known in the art (e.g., thermal bonds, radio frequency bonds, pressure bonds, ultrasonic bonds, welds, stitching, and the like). In some embodiments, the core assembly 23 is attached to the outer cover 24 in as few locations as possible; this can make the outer cover 24 look and feel softer. Suitable examples for attaching the core assembly to the outer cover include the attachment means described in U.S. Publication No. 2007/0287982 entitled "Disposable Wearable Absorbent Articles With Anchoring Systems," filed Nov. 15, 2006 by Richard Lodge, et al. Other Suitable examples for attaching the core assembly to the outer cover include the attachment means described U.S. Publication No. 2007/0287983 entitled "Absorbent Article Having An Anchored Core Assembly," filed Nov. 15, 2006 by Richard Lodge, et al.

On the other hand, in order to make the design more tamper-resistant, it may be desirable to attach the core assembly 23 to the outer cover 24 along at least part, if not all, of the core assembly's periphery; or a small distance (about 5-20 mm) inboard of the periphery. For example, the bond area between the core assembly 23 and the outer cover 24 can be less than about 70%, or, as another example, less than about 50%, or, as yet another example, less than about 20% of the core assembly 23 surface area that is attached to the BSOC 24.

The core assembly 23 is the portion of the diaper 20 providing much of the absorptive and containment function. The absorbent core assembly 23 includes an absorbent core 26, both of which can be disposed symmetrically or asymmetrically with respect to either or both of the longitudinal centerline 100 and/or the lateral centerline 110. As illustrated, the absorbent core 26 and core assembly 23 are symmetrical with respect to both the longitudinal centerline 100 and the lateral centerline 110.

The absorbent core 26 can include a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 26 can include (1) a fluid-acquisition component which acquires fluid exudates and partitions the exudates away from a wearer's body, (2) a fluid-distribution component which redistributes fluid exudates to locations displaced from the point of initial exudate loading, and/or (3) a fluid-storage component which retains a majority of the fluid exudates on a weight basis. A suitable absorbent core comprising an acquisition layer, a distribution layer, and/or a storage layer is described in U.S. Pat. No. 6,013,589. A suitable absorbent core having minimal absorbent fibrous material (i.e., not more than about 20 wt. % based on the weight of the absorbent core) within the absorbent core is described in U.S. 2004/0167486. Other suitable absorbent core configurations are discussed in U.S. 2003/0225382A1, U.S. 2006/0155253, and U.S. 2006/0155254.

In some embodiments, the core assembly 23 can include a containment member 28, such that the absorbent core 26 is disposed between the topsheet 22 and the containment member 28. In some embodiments, the containment member 28 covers a garment-facing surface of the absorbent core 26, at least in part, and extends laterally beyond the core 26. The containment member 28 can also extend upwardly to cover the lateral sides of the absorbent core 26. The containment member 28 can be constructed from a woven web, a nonwoven web (with synthetic and/or natural fibers), an apertured film, and a composite or laminate of any of the aforementioned materials. In certain embodiments, the containment member 28 is an air permeable nonwoven web such as described in U.S. Pat. No. 4,888,231.

The absorbent core assembly can also include a core cover 29 disposed on a wearer-facing surface of the absorbent core 26. The core cover 29 can help immobilize the liquid absorbent material of the absorbent core 26. The core cover 29 may generally be a liquid pervious material, such as a nonwoven material or tissue.

The components of the core assembly 23 can be joined as described via any suitable adhesive or cohesive or via any other suitable means known in the art. Any of the aforementioned layers of the core assembly 23 can be a single material or can be a laminate or other combination of two or more materials.

As illustrated, the topsheet 22 is a distinct structural unit that covers the absorbent core 23 and is attached to the BSOC 24, for example via the adhesive or cohesive 32, thereby forming an enclosure for the absorbent core. In an alternate embodiment (not shown), the core assembly 23 can be self-contained by integrating the topsheet 22 into the core assembly 23, for example by disposing the topsheet 22 adjacent a body-facing surface of the core cover 29. The topsheet 22 can be made from any suitable liquid-permeable material, for example those described in U.S. Pat. No. 3,860,003, U.S. Pat. No. 5,151,092, and U.S. Pat. No. 5,221,274.

As shown, a pair of opposing and longitudinally extending leg cuffs 35 are disposed on and extend outwardly from the topsheet 22. The leg cuffs 35 provide a seal against the wearer's body and improve containment of liquids and other body exudates. In the alternate embodiment (not shown) described above in which the core assembly 23 is self-contained and includes the topsheet 22, the leg cuffs 35 can simply be the extension of the laterally distal ends of the containment member 28.

The diaper 20 can also include a waistband 43 that generally forms at least a portion of the end edge 56 and/or a leg elastic (not shown) that generally forms at least a portion of the side edges 54. The waistband 43 and leg elastic are those portions of the diaper 20 which are intended to elastically expand and contract to dynamically fit the wearer's waist and legs, respectively, to provide improved fit and containment. The elastic waistband 43 can include a segment positioned in the front waist region 36 and/or the back waist region 38, and can be discretely attached or an integral part of the chassis 21. Examples of suitable waistbands include those described in U.S. Pat. No. 4,515,595, U.S. Pat. No. 5,151,092, and U.S. Pat. No. 5,221,274.

The diaper 20 can be preformed by the manufacturer to create a pull-on diaper or pant, and the diaper can be prefastened by the manufacturer or fastened by the consumer prior to wearing. Specifically, the diaper 20 may include left and right closed side seams 34, each disposed at regions proximal the front and back ends of side edges 54. Each side seam 34 can be closed by buttressing and subsequently attaching a given side edge 54 in the front and back waist regions 36 and 38 either using a permanent seam or refastenable closure member. Suitable permanent seams include, for example, heat seals, ultrasonic bonds, high pressure bonds, radio frequency bonds, hot air bonds, and heated point bonds. Suitable refastenable closure members include, for example, hook and loop fasteners, hook and hook fasteners, macrofasteners, tape fasteners, adhesive fasteners, cohesive fasteners, magnetic fasteners, hermaphrodidic fasteners, buttons, snaps, and tab and slot fasteners. The side edges 54 can alternatively be attached in an exterior surface-to-exterior surface configuration, interior surface-to-interior surface configuration, or interior surface-to-exterior surface (overlapping) configuration.

When in use, the pull-on diaper 20 is worn on the lower torso of a wearer, such that the end edges 56 encircle the waist of the wearer while, at the same time, the chassis side edges 54 define leg openings that receive the legs of the wearer. The crotch region 37 is generally positioned between the legs of the wearer, such that the absorbent core 26 extends from the front waist region 36 through the crotch region 37 to the back waist region 38.

In another embodiment (not shown), the principles of the present invention as described above with respect to pant-like garments can be equally applied to absorbent articles that are configured as taped diapers. In this embodiment, the diapers are not closed prior to wearing. Instead, the diapers generally include side panels having engaging elements. The side panels can be attached to the diaper chassis at either or both of the front and rear waist regions such that the engaging elements, when worn, contact some portion of the diaper on the opposing waist region to seal the diaper. Examples of suitable diapers according to the present invention are described in U.S. Publication No. 2008/0114326 entitled "Disposable Absorbent Article Having A Wrap And Tuck Configuration," filed Nov. 15, 2006 by Don Roe, et al.

Test Methods

Hysteresis Test

A commercial tensile tester (e.g., from Instron Engineering Corp. (Canton, Mass.) or SINTECH-MTS Systems Corporation (Eden Prairie, Minn.)) is used for this test. The instrument is interfaced with a computer for controlling the test speed and other test parameters, and for collecting, calculating and reporting the data. The hysteresis is measured under typical laboratory conditions (i.e., room temperature of about 20° C. and relative humidity of about 50%).

When a BSOC is analyzed according to the hysteresis test, a 2.54 cm (width)×7.62 cm (length) sample of the BSOC material is taken. The length of the BSOC sample is taken in the cross machine direction.

The procedure for determining hysteresis is as follows:
1. Select appropriate jaws and a load cell for the test. The jaws must be wide enough to fit the sample (e.g., at least 2.54 cm wide). The load cell is selected so that the tensile response from the sample tested will be between 25% and 75% of the capacity of the load cells or the load range used. A 5-10 kg load cell is typical.
2. Calibrate the tester according to the manufacturer's instructions.
3. Set the gauge length at 25 mm.
4. Place the sample in the flat surface of the jaws such that the longitudinal axis of the sample is substantially parallel to the gauge length direction.
5. Perform the hysteresis test with the following steps:
   a. First cycle loading: Pull the sample to 50% strain at a constant cross head speed of 254 mm/min.
   b. First cycle unloading: Hold the sample at 50% strain for 30 seconds and then return the crosshead to its starting position at a constant cross head speed of 254 mm/min. The sample is held in the unstrained state for 1 minute prior to measuring the first cycle % set. If the first cycle % set is not to be measured, the sample can be immediately subjected to the second cycle loading (i.e., nominally about 2 seconds after the first cycle unloading).
   c. Second cycle loading: Pull the sample to 50% strain at a constant cross head speed of 254 mm/min.
   d. Second cycle unloading: Hold the sample at 50% strain for 30 seconds and then return crosshead to its starting position at a constant cross head speed of 254 mm/min. The sample is held in the unstrained state for 1 minute prior to measuring the second cycle % set.

A computer data system records the force exerted on the sample during the loading and unloading cycles. From the resulting time-series (or, equivalently, distance-series) data generated, the % set can be calculated. The % set is the relative increase in strain after a given unloading cycle, and this value is approximated by the strain at 0.112 N, measured after the unloading cycle. For example, a sample with an initial length of 10 cm, a prestrain unload length of 15 cm (the prestrain unload length is applicable only to samples subjected to the prestrain cycle, which is described in more detail in example 3), a first unload length of 18 cm, and a second unload length of 20 cm would have a prestrain % set of 50% (i.e., (15-10)/10), a first cycle % set of 20% (i.e., (18-15)/15), and a second cycle % set of 11% (i.e., (20-18)/18). The nominal 0.112 N force is selected to be sufficiently high to remove the slack in a sample that has experienced some permanent plastic deformation in a loading cycle, but low enough to impart, at most, insubstantial stretch to the sample.

The hysteresis test can be suitably modified depending on the expected properties of the particular material measured. For instance, the hysteresis test can include only some of the loading cycles. Similarly, the hysteresis test can include different strains, such as, for example 75% strain, cross head speeds, and/or hold times. However, unless otherwise defined, the term "% set" as recited in the appended claims and examples refers to the first cycle % set as determined by the above loading cycles applied to an unactivated sample.

Tensile to Break Test

A commercial tensile tester (e.g., from Instron Engineering Corp. (Canton, Mass.) or SINTECH-MTS Systems Corporation (Eden Prairie, Minn.)) is used for this test. The instrument is interfaced with a computer for controlling the test speed and other test parameters, and for collecting, calculating and reporting the data. The Peak Elongation is measured under typical laboratory conditions (i.e., room temperature of about 20° C. and relative humidity of about 50%).

When a BSOC is analyzed according to the Tensile to Break test, a 2.54 cm (width)×7.62 cm (length) sample of the BSOC material is taken. The length of the BSOC sample is taken in the cross machine direction.

Procedure:
1. Select appropriate jaws and a load cell for the test. The jaws must be wide enough to fit the sample (e.g., at least 2.54 cm wide). The load cell is selected so that the tensile response from the sample tested will be between 25% and 75% of the capacity of the load cells or the load range used. A 5-10 kg load cell is typical.
2. Calibrate the tester according to the manufacturer's instructions.
3. Set the gauge length at 25 mm.
4. Place the sample in the flat surface of the jaws such that the longitudinal axis of the sample is substantially parallel to the gauge length direction.
5. Pull the sample at a constant cross head speed of 254 mm/min to about 1000% strain or until the sample exhibits a more than nominal loss of mechanical integrity.

A computer data system records the force exerted on the sample during the test as a function of applied strain. From the resulting data generated, the following quantities are reported:
1. Loads at 15%, 50% and 75% strain (N/cm)
2. Peak elongation (%) and peak load (N/cm)

Peak elongation is the strain at peak load. Peak load is the maximum load observed during the Tensile to Break test.

Hydrostatic Head (Hydrohead) Pressure

The property determined by this test is a measure of the liquid barrier property (or liquid impermeability) of a material. Specifically, this test measures the hydrostatic pressure the material will support when a controlled level of water penetration occurs. The hydrohead test is performed according to EDANA 120.2-02 entitled "Repellency: Hydrostatic Head" with the following test parameters. A TexTest Hydrostatic Head Tester FX3000 (available from Textest AG in Switzerland or from Advanced Testing Instruments in Spartanburg, S.C., USA) is used. For this test, pressure is applied to a defined sample portion and gradually increases until water penetrates through the sample. The test is conducted in a laboratory environment at about 22±2° C. temperature and about 50% relative humidity. The sample is clamped over the top of the column fixture, using an appropriate gasketing material (o-ring style) to prevent side leakage during testing. The area of water contact with the sample is equal to the cross sectional area of the water column, which equals 28 cm$^2$. Water inside the column is subjected to a steadily increasing pressure, which pressure increases at a rate of 20 mbar/min. When water penetration appears in three locations on the exterior surface of the sample, the pressure (measured in mbar) at which the third penetration occurs is recorded. If water immediately penetrates the sample (i.e., the sample provided no resistance), a zero reading is recorded. For each material, three specimens are tested and the average result is reported.

Moisture Vapor Transmission Rate Test

This method is applicable to thin films, fibrous materials, and multi-layer laminates of the foregoing. The method is based on ASTM Method E96-66. In the method, a known amount of a desiccant ($CaCl_2$) is put into a cup-like container. A sample of the outer cover material to be tested (sized to about 38 mm×64 mm, being sufficiently large to cover the opening of the desiccant container) is placed on the top of the container and held securely by a retaining ring and gasket. The assembly is placed in a constant temperature (40° C.) and humidity (75% RH) chamber for 5 hours. The amount of moisture absorbed by the desiccant is determined gravimetrically and used to calculate the moisture vapor transmission rate (MVTR) of the sample. The MVTR is the mass of moisture absorbed divided by the elapsed time (5 hours) and the open surface area at the interface between the container and the sample. The MVTR is expressed in units of g/m$^2$·day. A reference sample, of established permeability, is used as a positive control for each batch of samples. Samples are assayed in triplicate. The reported MVTR is the average of the triplicate analyses, rounded to the nearest 100 g/m$^2$·day. The significance of differences in MVTR values found for different samples can be estimated based on the standard deviation of the triplicate assays for each sample.

Opacity

The opacity value of a material is inversely proportional to the amount of light that can pass through the material. The opacity is determined from two reflectance measurements on a material sample.

To determine the opacity of an outer cover, an appropriately sized sample (based on the measurement opening of the color measurement instrument; about a 12 mm diameter for the instrument used herein) is cut from the outer cover and first backed with a black plate. A first color reading is taken with the black-backed sample to determine a first CIE tristimulus value $Y_1$. The black backing is removed and the sample is then backed with a white plate. A second color reading is taken with the white-backed sample to determine a second CIE tristimulus value $Y_2$. The opacity is expressed as the ratio of the two readings: Opacity (%)=$Y_1/Y_2 \times 100\%$. The opacity values reported herein were determined with a HUNTERLAB LABSCAN XE (model LSXE, available from Hunter Associates Laboratory, Inc., Reston, Va.). However, other instruments capable of determining CIE tristimulus values are also suitable.

EXAMPLES

In the following, the properties for each sample prepared for a given example are not necessarily reported for each sample parameter measured. In such case, the omission of a sample from a particular data table indicates that the omitted sample was not evaluated for the properties listed in the data table.

Example 1

Sample 1A was a spunbond material formed from a layer of elastomeric fibers ("$S_{el}$"; V2120 fiber-grade VISTAMAXX elastomeric polypropylene) having a basis weight of 30 g/m². Sample 1B was a composite nonwoven material formed from a layer of elastic meltblown fibers ("$M_{el}$"; V2120 elastomeric polypropylene) having a basis weight of 4 g/m² in between two layers of elastic spunbond fibers (V2120 elastomeric polypropylene) each having a basis weight of 15 g/m². The spunbond and meltblown fibers had nominal diameters of about 20 µm or more and about 1 µm, respectively.

Samples 1A and 1B were activated in a hydraulic press using a set of flat plates (pitch of 0.100" or 2.5 mm), to a depth of engagement of about 2.5 mm in either the CD only or in both MD and CD. FIGS. 1 and 2 are the SEMs of Sample 1B prior to and after activation, respectively. The changes in sample dimensions produced during mechanical activation were subsequently subjected to a hysteresis test to determine the post-activation, first cycle % set. The results are summarized in Table 1.

TABLE 1

| Sample | Material | Basis Weight | % Set (CD) After Activation in CD | % Set (CD) After Activation in MD/CD |
|---|---|---|---|---|
| 1A | $S_{el}$ | 30 g/m² | 21.0% | 21.3% |
| 1B | $S_{el}M_{el}S_{el}$ | 34 g/m² | 11.0% | 11.9% |

The results in Table 1 illustrate the ability of the interlayer meltblown fibers to increase the ability of the nonwoven to undergo recovery of the BSOC by substantially reducing the % set produced during activation. They suggest that the meltblown layer helps maintain the mechanical integrity of the nonwoven material during mechanical activation. In both cases, the softness of the nonwoven material is improved after activation.

Example 2

Sample 2A was a spunbond material formed from two superimposed layers of elastomeric fibers (V2120 fiber-grade VISTAMAXX elastomeric polypropylene) each having a basis weight of 30 g/m². Sample 2B was a thermally bonded composite nonwoven material formed from a layer of elastic nanofibers ("$N_{el}$"; V2120 elastomeric polypropylene) having a basis weight of 5 g/m² in between two layers of elastic spunbond fibers (V2120 elastomeric polypropylene) each having basis weight of 30 g/m². The spunbond and meltblown fibers had nominal diameters of about 20 µm or more and less than about 1 µm, respectively.

Samples 2A and 2B were analyzed according to the opacity test. FIG. 3 is the SEM of Sample 2B prior to mechanical activation. The results are summarized in Table 2.

TABLE 2

| Sample | Material | Basis Weight | Opacity (%) |
|---|---|---|---|
| 2A | $S_{el}$ | 60 g/m² | 43% |
| 2B | $S_{el}N_{el}S_{el}$ | 65 g/m² | 52% |

The results in Table 2 illustrate the ability of the interlayer nanofibers to improve the aesthetic properties of the BSOC by substantially increasing the opacity of the nonwoven material. Based on this data, a projected total of about 10 g/m² to about 20 g/m², for example about 15 g/m² of meltblown fibers would suffice to reach an opacity of at least about 65% for the nonwoven material, prior to activation, in the relaxed state.

Example 3

The samples of Example 3 illustrate the tensile properties of nonwoven plastoelastic materials formed from a mixture of elastomeric fibers (V2120 fiber-grade VISTAMAXX elastomeric polypropylene) and plastic fibers (polyolefin-based). Table 3A lists the various samples tested, the approximate relative amounts of elastomeric fibers and plastic fibers in each sample, and the nominal basis weights of the mixed fiber sample.

TABLE 3A

| Sample | Nominal Basis Weight | Elastomeric Component | Plastic Component |
|---|---|---|---|
| 3A | 25 g/m² | 100 wt. % | 0 wt. % |
| 3B | 25 g/m² | 50 wt. % | 50 wt. % |
| 3C | 35 g/m² | 50 wt. % | 50 wt. % |
| 3D | 45 g/m² | 50 wt. % | 50 wt. % |
| 3E | 25 g/m² | 58 wt. % | 42 wt. % |
| 3F | 35 g/m² | 58 wt. % | 42 wt. % |
| 3G | 45 g/m² | 58 wt. % | 42 wt. % |

The tensile properties of Samples 3B-3G were tested after activation in both the CD and MD using a set of flat plates placed in a hydraulic press. Activation was performed at intermediate strain rate values, such as, for example strain rates of between about 1 sec⁻¹ and about 50 sec⁻¹, and a depth of engagement of about 2.5 mm. Table 3B summarizes results of the tensile property testing in terms of the sample tested, its actual basis weight, and the direction in which the tensile property was determined. The tensile properties were determined according to the methods described herein.

TABLE 3B

| Sample | Actual Basis Weight | Direction | Peak Load (N/cm) | Peak Stress (MPa) | Strain at Break (%) |
|---|---|---|---|---|---|
| 3B | 25 g/m² | CD | 2.47 | 9.07 | ~300–400 |
| 3C | 36 g/m² | CD | 4.21 | 10.3 | 326 |
| 3D | 49 g/m² | CD | 5.43 | 10.0 | ~300–400 |
| 3E | 26 g/m² | CD | 2.01 | 7.00 | ~350–400 |
| 3E | 25 g/m² | MD | 5.71 | 21.1 | 235 |
| 3F | 36 g/m² | CD | 3.60 | 8.84 | 329 |
| 3G | 46 g/m² | CD | 4.99 | 9.60 | 285 |

Samples 3A and 3E were also subjected a hysteresis test, the results of which are shown in Table 3C. The "% set" value is the first cycle % set. The samples were subjected to the hysteresis test as described in the Test Methods section, except that the samples were pulled and held at 75% strain rather than 50% during the first and second loading and unloading cycles. Prior to running the hysteresis test, the unactivated sample was prestrained by subjecting the unactivated sample to a prestrain cycle. The prestrain cycle involved pulling the unactivated sample to 200% strain at a constant cross head speed of 254 mm/min (10 inch/min), and then, without holding the sample in the elongated state for more than a nominal amount of time (for example, about 2 seconds), returning the cross head to its starting position at a constant cross head speed of 254 mm/min. The prestrained sample remained in this unstrained state for 1 minute, after which time the prestrain % set can be measured.

The "maximum load" value represents either the force at 200% strain for the unactivated sample during the prestrain cycle or the force at 75% strain for the activated samples during the first loading cycle. The activated samples were tested after activation in both the CD and MD in a benchtop hydraulic press having a depth of engagement of about 2.5 mm.

TABLE 3C

| Sample | Act.? | Actual Basis Weight | % Set | 1st Strain Cycle | | | 2nd Strain Cycle | |
|---|---|---|---|---|---|---|---|---|
| | | | | Maximum Load | 50% Load | 75% Relax. | 20% Load | 75% Relax. |
| 3A | N | 25 g/m² | 33.4 | 3.09 N | 0.37 N | 46.5% | 0.04 N | 36.2% |
| 3A | Y | 18 g/m² | 17.2 | 0.64 N | 0.26 N | 50.6% | 0.03 N | 35.5% |
| 3E | Y | 24 g/m² | 25.7 | 0.64 N | 0.25 N | 47.9% | 0.01 N | 33.7% |

Samples 3E-3G were also subjected to a high strain rate activation test, using a High-Speed Research Press ("HSRP"). During the test, the force applied to a nonwoven material sample was measured while the material was elongated up to a strain of 1000% at strain rates up to 1000 s$^{-1}$ using two flat ring-roll plates having a depth of engagement of about 8.2 mm and a pitch of about 1.5 mm. The samples were essentially completely shredded at the end of the test. The resulting data (i.e., applied force as a function of strain at a fixed strain rate) were analyzed to identify the strain at which the applied force was at a maximum. When the normalized applied force (i.e., applied force per unit weight of the nonwoven sample) is at a maximum, the nonwoven material loses its ability to withstand additional loading without an increased likelihood of material destruction. The strain at the maximum applied force represents the ability of the nonwoven material to withstand the mechanical activation process having approximately the same degree of strain. Table 3D summarizes the results of these tests.

TABLE 3D

| Sample | Strain Rate | Strain Direction | Maximum Applied Force | Strain at Max. Force |
|---|---|---|---|---|
| 3E | 1000 s$^{-1}$ | CD | 17 kN/g | 200% |
| 3F | 1000 s$^{-1}$ | CD | 18 kN/g | 200% |
| 3G | 1000 s$^{-1}$ | CD | 19 kN/g | 190% |
| 3E | 500 s$^{-1}$ | MD | 35 kN/g | 180% |
| 3E | 500 s$^{-1}$ | CD | 15 kN/g | 280% |

The results in Table 3D suggest that the plastoelastic materials of the present disclosure are capable of withstanding a mechanical activation process at strain levels up to about 200%, for example up to about 300%, while incurring only minimal damage, even at very high strain rate conditions. This is in contrast to typical commercial extensible nonwoven materials that can only withstand strains up to about 150% when subjected to comparable strain rates.

Figure 6:
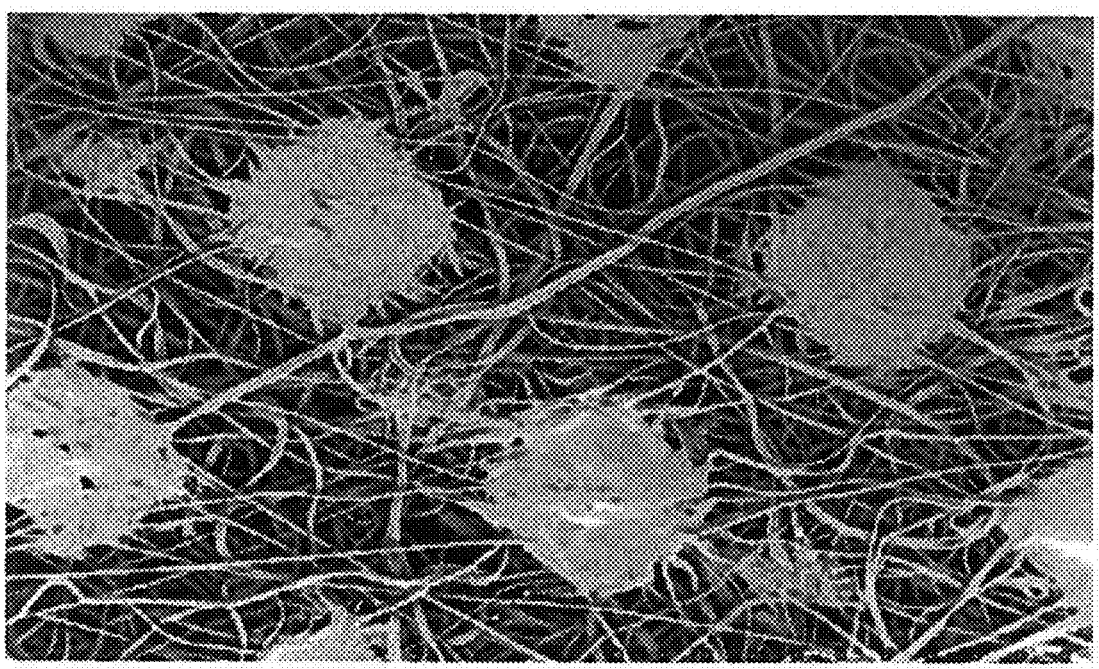
FIG. 6 is a top view from a scanning electron micrograph of a plastoelastic nonwoven material prior to mechanical activation.
Figure 7:
FIG. 7 is a side view from a scanning electron micrograph of the plastoelastic nonwoven material of FIG. 6 prior to mechanical activation.
Figure 8:
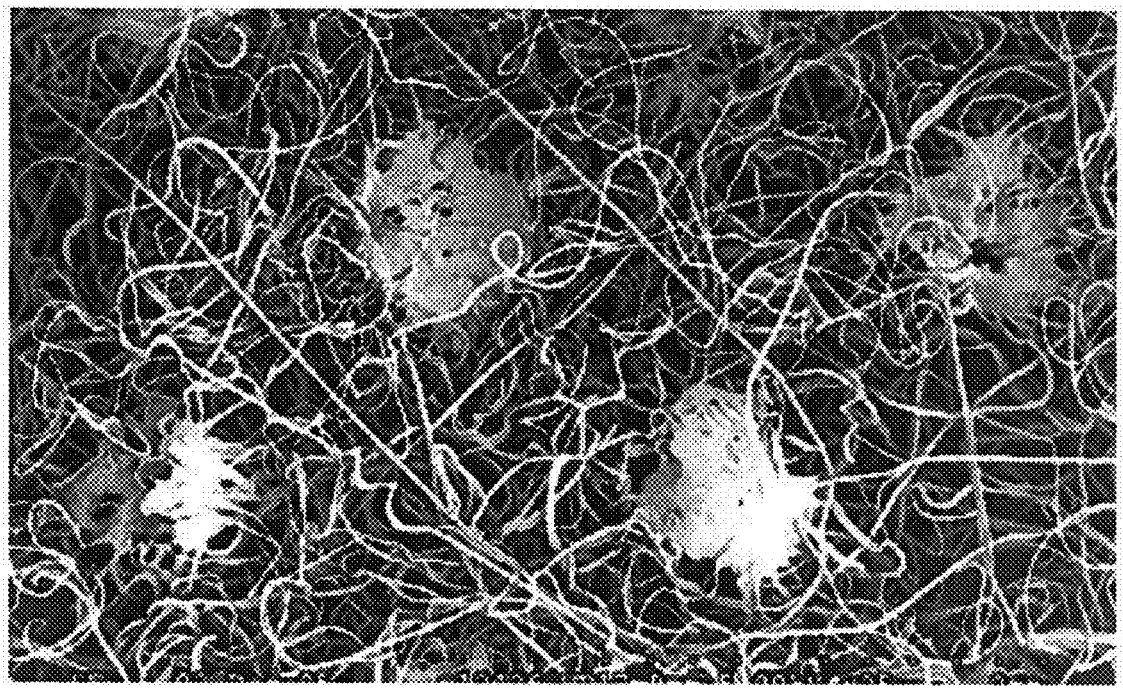
FIG. 8 is a top view from a scanning electron micrograph of the plastoelastic nonwoven material of FIG. 6 after mechanical activation.
Figure 9:
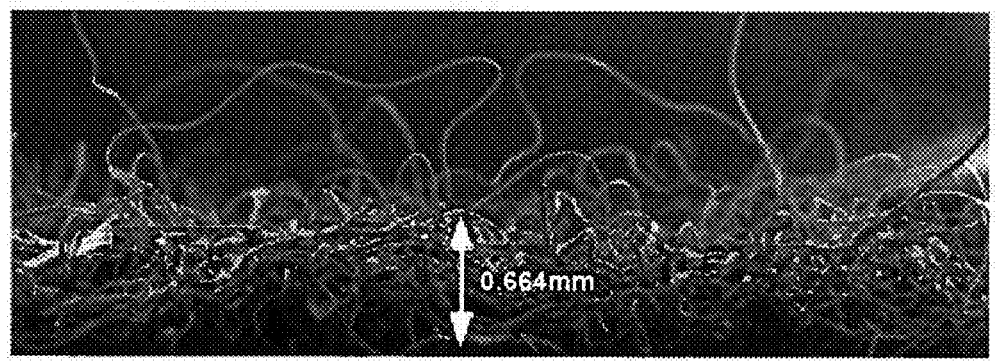
FIG. 9 is a side view from a scanning electron micrograph of the plastoelastic nonwoven material of FIG. 6 after mechanical activation.

The activation process also improves the softness and feel of the plastoelastic nonwoven material. This effect is largely related to the increase in web loft/thickness created during the activation process. FIGS. 6-9 illustrate this effect for the nonwoven plastoelastic materials of Example 3. FIGS. 6 and 7 are SEMs of a bonded plastoelastic nonwoven material prior to activation (top and side views, respectively). FIGS. 8 and 9 are SEMs of the same nonwoven material after activation (top and side views, respectively), and they illustrate the increased thickness of the material.

Example 4

The samples of Example 4 illustrate the tensile properties of composite nonwoven plastoelastic materials formed from a layer of plastoelastic bi-component spunbond fibers and a layer of elastic spunbond fibers. V2120 fiber-grade VISTAMAXX elastomeric polypropylene was used as the elastic component of the bi-component fibers and for the elastic fibers themselves. For samples 4A-4D, the plastic component of the bi-component fibers was a mixture of PH-835 Ziegler-based polypropylene (50 wt. %; available from Basell Polyolefins, Elkton, Md.) and HH-441 high melt flow rate polypropylene (50 wt. %; melt flow rate=400 g/10 minutes; available from Himont Co., Wilmington, Del.). For samples 4E-4G, the plastic component of the bi-component fibers was a Basell Moplen 1669 random polypropylene copolymer with a small amount of polyethylene (also available from Basell Polyolefins). The bi-component fibers had an elastomeric core and a plastic sheath, and the weight fraction of each component is given in Table 4. The elastic fibers also contained about 3.5 wt. % of an anti-blocking agent to improve their spinning performance. Each of the two spunbond layers represents about half of the total basis weight of the nonwoven material (i.e., the value listed in the second column of Table 4). The two spunbond layers were thermally bonded using two heated rolls, with the first at 84° C., and the second at 70° C.

Table 4 summarizes the tensile properties of the spunbond-spunbond composites tested in an unactivated state. The properties were determined with standard EDANA methods (EDANA method 40.3-90 for the basis weight and EDANA method 20.2-89 for the tensile properties).

Table 4 also summarizes the properties of the composites tested after a modified hysteresis test. The hysteresis test described in the "Test Methods" section above was modified in the following aspects: (1) sample size (5 cm wide×15 cm long), (2) crosshead speed (500 mm/min), and (3) first and second cycle loading/unloading (100% maximum strain, held for 1 second at maximum strain, held for 30 seconds after unloading). For each cycle, Table 4 provides the force at 100% strain (normalized by the sample width) and the % set after unloading. For the first cycle, the % set is the strain after the first cycle unloading measured at 0.112 N. For the second cycle, the % set is the relative increase in strain between the unloaded states of the first and second cycles, measured at 0.112 N after completing the second cycle unloading. For example, a sample with an initial length of 10 cm, a first unload length of 15 cm, and a second unload length of 18 cm would have a first cycle % set of 50% and a second cycle % set of 20%.

TABLE 4

| Sample | Basis Wt. (g/m²) | Core/Sheath Weight Ratio (%/%) | Tensile Stress (N/50 mm) CD | Tensile Stress (N/50 mm) MD | Elongation (%) CD | Elongation (%) MD | Load at 100% Strain (N/50 mm) 1st Cycle | Load at 100% Strain (N/50 mm) 2nd Cycle | % Set 1st Cycle | % Set 2nd Cycle |
|---|---|---|---|---|---|---|---|---|---|---|
| 4A | 37.5 | 80/20 | 11.9 | 17.9 | 106 | 101 | 11.4 | 9.58 | 70 | 17 |
| 4B | 38.8 | 90/10 | 8.50 | 12.8 | 152 | 155 | 7.68 | 6.76 | 59 | 19 |
| 4C | 58.7 | 80/20 | 20.2 | 29.2 | 133 | 139 | 18.7 | 16.4 | 68 | 20 |
| 4D | 60.7 | 90/10 | 18.7 | 24.2 | 144 | 133 | 14.4 | 12.7 | 57 | 21 |
| 4E | 44.8 | 90/10 | 8.00 | 11.0 | 145 | 133 | 6.70 | 5.80 | 45 | 8 |
| 4F | 66.7 | 90/10 | 14.6 | 18.7 | 158 | 146 | 12.9 | 11.0 | 52 | 16 |
| 4G | 59.7 | 80/20 | 18.0 | 24.8 | 102 | 100 | 18.1 | 15.7 | 61 | 17 |

The results in Table 4 indicate that a mechanically activated BSOC formed from the plastoelastic materials of the present disclosure has favorable stretch properties, and would be able to exhibit % set values less than about 20%, and as low as less than about 10%.

Example 5

The samples of Example 5 illustrate the tensile properties of plastoelastic film materials formed with an elastomeric component (V1100 film-grade VISTAMAXX elastomeric polypropylene), plastic components (polyolefin-based), and an optional opacifier. The various plastic components are summarized in Table 5A and include linear low density polyethylene (LL6201), low molecular weight polyethylene waxes (A-C 617, A-C 735, and PARVAN 1580), and a low molecular weight polypropylene wax (LICOWAX PP230). The unactivated samples were tested to determine their tensile properties and then subjected to a modified hysteresis test (including only a prestrain cycle, as described in Example 3, and a first cycle loading/unloading), the results of which are provided in Tables 5B and 5C.

TABLE 5A

| Sample | V1100 (wt. %) | LL6201 (wt. %) | AC 735 (wt. %) | AC 617 (wt. %) | P. 1580 (wt. %) | PP 230 (wt. %) | TiO₂ (wt. %) |
|---|---|---|---|---|---|---|---|
| 5A | 60 | 10 | 10 | | | 20 | |
| 5B | 60 | 10 | | 10 | | 20 | |
| 5C | 60 | 10 | | | 10 | 20 | |
| 5D | 58.8 | 9.8 | | | 9.8 | 19.6 | 2.0 |
| 5E | 85 | 15 | | | | | |

TABLE 5B

| Sample | Basis Weight | Direction | Peak Load (N/cm) | Peak Stress (MPa) | Strain at Break (%) |
|---|---|---|---|---|---|
| 5A | 16 g/m² | CD | 6.8 | 15 | 741 |
| 5B | 24 g/m² | CD | 10.5 | 14 | 636 |
| 5C | 19 g/m² | CD | 8.0 | 15 | 755 |
| 5E | 29 g/m² | CD | 20.7 | 23 | 848 |

TABLE 5C

| Sample | Film Thickness | Basis Weight | % Set | 1st Strain Cycle Prestrain 200% Load | 50% Load | 50% Relax. | 30% Unload |
|---|---|---|---|---|---|---|---|
| 5A | 13 μm | 16 g/m² | 33.7 | 1.36 N | 0.6 N | 31.5% | 0.15 N |
| 5B | 22 μm | 24 g/m² | 27.3 | 2.07 N | 0.9 N | 30.7% | 0.25 N |
| 5C | 20 μm | 20 g/m² | 41.8 | 2.03 N | 0.9 N | 33.9% | 0.20 N |
| 5D | 25 μm | 24 g/m² | 32.3 | 2.50 N | 1.1 N | 32.7% | 0.23 N |
| 5E | 13 μm | 14 g/m² | 32.0 | 1.50 N | 0.5 N | 76.1% | 0.05 N |

The results in Table 5A-5C illustrate that the plastoelastic film formulations of the present disclosure have favorable mechanical properties that make them suitable for inclusion into a BSOC.

Example 6

The samples of Example 6 illustrate the tensile properties of an elastic film formed with elastomeric components, anti-blocking agents, and an opacifier (titanium dioxide). The various components are summarized in Table 6A and include elastomeric polypropylene (V1100 film-grade VISTAMAXX), styrenic block copolymers (VECTOR V4211 and PS3190 (available from Nova Chemicals, Pittsburgh, Pa.)), a soft polypropylene-based thermoplastic elastomer reactor blend (ADFLEX 7353, available from Basell Polyolefins, Elkton, Md.), and anti-blocking agents (CRODAMIDE and INCROSLIP, both available from Croda, Inc., Edison, N.J.). The unactivated samples were tested to determine their tensile properties and then subjected to a modified hysteresis test (including only a prestrain cycle, as described in Example 3, and a first cycle loading/unloading), the results of which are provided in Tables 6B and 6C.

TABLE 6A

| Sample | V1100 (wt. %) | V4211 (wt. %) | PS3190 (wt. %) | Adflex (wt. %) | Crodamide (wt. %) | Incroslip B (wt. %) | TiO$_2$ (wt. %) |
|---|---|---|---|---|---|---|---|
| 6A | 41.7 | 37.0 | 6.5 |  | 5.55 | 5.55 | 3.7 |
| 6B | 75.6 |  |  | 8.4 | 5.5 | 6.8 | 3.7 |
| 6C | 85.7 |  |  |  | 4.0 | 6.7 | 3.6 |

TABLE 6B

| Sample | Basis Weight | Direction | Peak Load (N/cm) | Peak Stress (MPa) | Strain at Break (%) |
|---|---|---|---|---|---|
| 6A | 31 g/m$^2$ | CD | 16.5 | 21 | 731 |
| 6B | 25 g/m$^2$ | CD | 11.0 | 15 | 623 |

TABLE 6C

| | | | | 1$^{st}$ Strain Cycle | | | |
|---|---|---|---|---|---|---|---|
| Sample | Film Thickness | Basis Weight | % Set | Prestrain 200% Load | 50% Load | 50% Relax. | 30% Unload |
| 6A | 25 µm | 31 g/m$^2$ | 11.6 | 2.30 N | 1.17 N | 21.6% | 0.51 N |
| 6B | 20 µm | 21 g/m$^2$ | 14.8 | 1.70 N | 0.90 N | 21.1% | 0.39 N |
| 6C | 20 µm | 21 g/m$^2$ | 19.2 | 1.86 N | 0.90 N | 23.1% | 0.35 N |

The results in Tables 6A-6C illustrate that the elastic film formulations of the present disclosure have favorable mechanical properties that make them suitable for inclusion into a BSOC when combined with a nonwoven material into a laminate structure.

Example 7

The samples of Example 7 illustrate the effect of including a plasticizer on the tensile properties of an elastic film. The various components are summarized in Table 7A. The plasticizer used was mineral oil, and the mineral oil was added to the formulation by heating the V1100 elastomeric polypropylene at 50° C. while in contact with the oil. The unactivated samples were then subjected to a modified hysteresis test (including only a prestrain cycle, as described in Example 3, and a first cycle loading/unloading), the results of which are provided in Table 7B.

TABLE 7A

| Sample | V1100 (wt. %) | Min. Oil (wt. %) | Crodamide (wt. %) | Incroslip B (wt. %) | TiO$_2$ (wt. %) |
|---|---|---|---|---|---|
| 7A | 80 |  | 6 | 6 | 8 |
| 7B | 60 | 20 | 6 | 6 | 8 |

TABLE 7B

| | | | | 1$^{st}$ Strain Cycle | | | |
|---|---|---|---|---|---|---|---|
| Sample | Film Thickness | Basis Weight | % Set | Prestrain 200% Load | 50% Load | 50% Relax. | 30% Unload |
| 7A | 20 µm | 21 g/m$^2$ | 19.2 | 1.86 N | 0.9 N | 23.1% | 0.35 N |
| 7B | 15 µm | 14 g/m$^2$ | 17.9 | 0.48 N | 0.2 N | 17.8% | 0.11 N |

The results in Tables 7A-7B illustrate that the inclusion of a plasticizer into the film formulations of the present disclosure can substantially reduce the loading/unloading forces while retaining favorable % set values.

Example 8

The samples of Example 8 illustrate the effect of including filler particles on the breathability and the tensile properties of a plastoelastic film formed with an elastomeric component (V1100 film-grade VISTAMAXX elastomeric polypropylene and, optionally, VECTOR V4211 styrenic block copolymer), a plastic component (LL6201 linear low density polyethylene), calcium carbonate filler particles, and titanium dioxide opacifying particles. The samples were tested after activation in the CD only at strain rates of about 500 s$^{-1}$ and a depth of engagement of about 4.4 mm for a pitch of about 3.8 mm (0.150"). The formulations and resulting properties are show in Tables 8A and 8B. The samples listed in Table 8B were subjected to a modified hysteresis test (including only a prestrain cycle, as described in Example 3 and a first cycle loading/unloading).

TABLE 8A

| Sample | V1100 (wt. %) | V4211 (wt. %) | LL6201 (wt. %) | CaCO$_3$ (wt. %) | TiO$_2$ (wt. %) | Film Thickness (µm) | MVTR (g/m$^2$ · d) |
|---|---|---|---|---|---|---|---|
| 8A | 30 |  | 20 | 48 | 2 | 30 | 1727 |
| 8B | 32 |  | 16 | 50 | 2 | 30 | 2064 |
| 8C | 33 |  | 13 | 52 | 2 | 46 | 1746 |
| 8D | 34 |  | 10 | 54 | 2 | 33 | 1908 |
| 8E | 35 |  | 7 | 56 | 2 | 30 | 1056 |
| 8F | 38 |  |  | 60 | 2 | 48 | 206 |
| 8G | 37 |  | 10 | 51 | 2 | 25 | 348 |
| 8H | 44 |  | 10 | 44 | 2 | 25 | 197 |
| 8I | 42 |  | 10 | 46 | 2 | 38 | 209 |
| 8J | 28 | 6 | 10 | 54 | 2 | 25 | 2989 |

TABLE 8B

| | | | 1$^{st}$ Strain Cycle | | | |
|---|---|---|---|---|---|---|
| Sample | Basis Weight | % Set | Prestrain 200% Load | 50% Load | 50% Relax. | 30% Unload |
| 8A | 43 g/m$^2$ | 55.3 | 3.31 N | 2.0 N | 33.9% | 0.26 N |
| 8B | 41 g/m$^2$ | 51.1 | 3.22 N | 1.8 N | 33.4% | 0.26 N |
| 8C | 59 g/m$^2$ | 65.5 | 4.02 N | 2.6 N | 35.9% | 0.36 N |
| 8D | 48 g/m$^2$ | 36.3 | 2.93 N | 1.3 N | 31.2% | 0.29 N |
| 8E | 42 g/m$^2$ | 30.0 | 2.30 N | 1.0 N | 28.9% | 0.27 N |
| 8F | 68 g/m$^2$ | 26.1 | 3.34 N | 1.4 N | 28.0% | 0.43 N |

The results in Tables 8A-8B illustrate that the inclusion of filler particles into the film formulations of the present disclosure can substantially increase the breathability of the film while retaining favorable mechanical properties.

Example 9

Example 9 illustrates the tensile properties of several nonwoven materials as well as two laminates suitable for use in outer covers according to the invention. The various properties are summarized in Tables 9A and 9B. Sample 1 is a trilaminate of a 24 gsm Vistamaxx film laminated to two layers of a 22 gsm extensible spunbond polypropylene (Softspan 200 from BBA, Simpsonville, S.C.). The Vistamaxx film comprises 84% of VM1100 from Exxon-Mobil, 8% titanium dioxide and 8% antiblock. This Vistamaxx film had no apertures and was non-breathable. An elastomeric adhesive (H2031 from Bostik Findley) was applied to either side of the Vistamaxx film at a basis weight of 9 gsm each side in order to laminate the film to the two nonwovens. The trilaminate was then incrementally stretched in the cross machine direction in a hydraulic press at a low strain rate (for example, <1 sec$^{-1}$) using activation plates with teeth having a pitch of 0.100 inches and a depth of engagement of 0.158 inches (Harrington Product Development, Cincinnati, Ohio). Sample 2 is a trilaminate similar to Sample 1, except that the Vistamaxx film had a basis weight of 15 gsm. Sample 3 is an 18.6 gsm spunbond nonwoven available from BBA (BBA, Simpsonville, S.C.). Sample 4 is 22 gsm Softspan 200 (BBA, Simpsonville, S.C.), which is an extensible spunbond nonwoven made with polyolefin fibers. Sample 5 is a 27 gsm HEC (High Elongation Carded, BBA, Simpsonville, S.C.), which is an extensible carded nonwoven made with polyolefinic fibers.

TABLE 9A

| Sample | Average Peak Elongation (%) |
|---|---|
| 3 | 84 |
| 4 | 228 |
| 5 | 199 |

Table 9A shows the average peak elongation of samples 3-5, measured according to the Tensile to Break test described herein. Five iterations of the Tensile to Break test were run on each sample with the peak elongation recorded for each test run. The average peak elongation for each sample was then calculated by adding together the five individual peak elongations and dividing the sum by five.

TABLE 9B

| Sample | Strain (%) | Load (N/cm) | Average Peak Elongation (%) | 1$^{st}$ Cycle % Set |
|---|---|---|---|---|
| 1 | 15 | 0.18 | 394 | 9 |
|  | 25 | 0.28 |  |  |
|  | 50 | 0.38 |  |  |
|  | 75 | 0.44 |  |  |
|  | 100 | 0.50 |  |  |
| 2 | 15 | 0.10 | 374 | 12 |
|  | 25 | 0.17 |  |  |
|  | 50 | 0.25 |  |  |
|  | 75 | 0.30 |  |  |
|  | 100 | 0.34 |  |  |

Table 9B shows the loads at various strains for Samples 1 and 2 that were observed during the Tensile to Break test. Also shown are the peak elongation values for Samples 1 and 2, measured according to Tensile to Break test. Five iterations of the Tensile to Break test were run on each sample with the peak elongation recorded for each test run. The average peak elongation for each sample was then calculated by adding together the five individual peak elongations and dividing the sum by five. Additionally, the 1$^{st}$ cycle % set values are shown for Samples 1 and 2, measured according to the Hysteresis test. Accordingly, the first cycle % set values were measured as the strain at 0.112 N after completing the first cycle unloading.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An outer cover for an absorbent article, the outer cover comprising:
   (a) a first layer of nonwoven fibers having a first number-average fiber diameter, the nonwoven fibers of the first layer including core-sheath type bi-component fibers wherein the bi-component fibers comprise a core formed from elastomeric polypropylene and a sheath formed from polyethylene;
   (b) a second layer of nonwoven fibers having a second number-average fiber diameter less than the first number-average fiber diameter, the second layer of nonwoven fibers disposed on the first layer of nonwoven fibers such that at least some of the fibers from the second layer are in contact with at least some of the fibers of the first layer;
   wherein the outer cover has been mechanically deformed;
   wherein the first layer of nonwoven fibers comprises spunbond fibers and the second layer of fibers comprises elastomeric and plastic nanofibers; and
   wherein the outer cover has a first cycle % set of about 20% or less as determined by the hysteresis test with 75% maximum strain.

2. The outer cover of claim 1, wherein the first fiber layer has a peak elongation of greater than about 100%.

3. The outer cover of claim 1, wherein the first fiber layer has a peak elongation of greater than about 120%.

4. The outer cover of claim 1, wherein the first fiber layer has a peak elongation of greater than about 150%.

5. The outer cover of claim 1, wherein the first number-average fiber diameter is about 10 μm to about 30 μm.

6. The outer cover of claim 1, wherein the first number-average fiber diameter is about 10 microns to about 30 microns and the second number-average fiber diameter is about 0.1 microns to about 1 microns.

7. The outer cover of claim 1, wherein the outer cover has a moisture vapor transmission rate of about 1,000 g/m$^2$·day to about 10,000 g/m$^2$·day.

8. The outer cover of claim 1, wherein the outer cover has an opacity of at least about 65%.

9. The outer cover of claim 1, wherein the outer cover has a hydrostatic head pressure of about 80 mbar or less.

10. The outer cover of claim 1, wherein the outer cover has a first cycle % set of about 20% or less as determined by subjecting an unactivated sample of the outer cover to the hysteresis test.

11. The outer cover of claim 1, wherein the outer cover has a tensile strain at breaking of about 200% to about 600%.

12. An absorbent article for receiving and storing bodily exudates, the absorbent article comprising:
(a) a liquid permeable nonwoven topsheet comprising a plurality of fibers;
(b) a multilayered outer cover comprising:
(i) a first layer comprising spunbond fibers, the fibers including core-sheath type bi-component fibers, wherein the bi-component fibers comprise a core formed from elastomeric polypropylene, and a sheath formed from polyethylene,
(ii) a second layer comprising meltblown elastomeric fibers, the second layer being disposed on the first layer,
(iii) a third layer comprising meltblown plastoelastic fibers, the third layer disposed between the second layer and a fourth layer,
(iv) the fourth layer comprising spunbond fibers, the fibers selected from the group consisting of plastic fibers and plastoelastic blend fibers, the fourth layer disposed on the third layer;
(v) a fifth layer, the fifth layer including elastomeric and plastic nanofibers disposed on the fourth layer,
(c) an absorbent core disposed between the topsheet and the outer cover;
wherein the outer cover is rendered stretchable using a mechanical activation process; and
wherein the outer cover has a first cycle % set of about 20% or less as determined by the hysteresis test with 75% maximum strain.

13. The absorbent article of claim 12, wherein:
the first and fifth layers of the outer cover each independently have a basis weight of about 10 g/m² to about 50 g/m²;
the second, third, and fourth layers of the outer cover each independently have a basis weight of about 1 g/m² to about 7 g/m²; and,
the outer cover having a net basis weight of about 25 g/m² to about 100 g/m².

14. The absorbent article of claim 12, wherein at least one of the first, second, third, fourth, and fifth layers is pre-stretched prior to an adjacent layer being disposed on the pre-stretched layer.

15. The absorbent article of claim 12, wherein the outer cover has a cross direction, and the outer cover has been activated in the cross direction.

16. The absorbent article of claim 12, wherein the outer cover has a machine direction, and the outer cover has been activated in the machine direction.

17. The absorbent article of claim 12, wherein the outer cover has been activated in at least one region and remains unactivated in at least one other region.

18. The absorbent article of claim 12, wherein the elastomeric fibers of the second layer include an elastomeric polypropylene selected from the group consisting of an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene, a metallocene polypropylene, and combinations thereof.

19. The absorbent article of claim 12, wherein the outer cover has a moisture vapor transmission rate of about 1,000 g/m²·day to about 10,000 g/m²·day.

20. The absorbent article of claim 12, wherein the outer cover has an opacity of at least about 65%.

21. The absorbent article of claim 12, wherein the outer cover has a hydrostatic head pressure of about 80 mbar or less.

22. The absorbent article of claim 12, wherein the outer cover has a first cycle % set of about 20% or less as determined by subjecting an unactivated sample of the outer cover to the hysteresis test.

23. The absorbent article of claim 12, wherein the outer cover has a tensile strain at breaking of about 200% to about 600%.

* * * * *